(12) United States Patent
Shintou et al.

(10) Patent No.: US 12,098,288 B2
(45) Date of Patent: Sep. 24, 2024

(54) COMPOUND, INK, RESIST COMPOSITION FOR COLOR FILTER, COLOR FILTER, SHEET FOR THERMAL TRANSFER RECORDING, AND TONER

(71) Applicant: CANON KABUSHIKI KAISHA, Tokyo (JP)

(72) Inventors: Taichi Shintou, Saitama (JP); Koromo Shirota, Kanagawa (JP); Ai Hayakawa, Kanagawa (JP); Tsuyoshi Santo, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 802 days.

(21) Appl. No.: 17/134,906

(22) Filed: Dec. 28, 2020

(65) Prior Publication Data
US 2021/0115259 A1 Apr. 22, 2021

Related U.S. Application Data

(63) Continuation of application No. PCT/JP2019/028485, filed on Jul. 19, 2019.

(30) Foreign Application Priority Data

Jul. 30, 2018 (JP) .................................. 2018-142389

(51) Int. Cl.
| | | |
|---|---|---|
| *C09B 55/00* | (2006.01) | |
| *B41M 5/39* | (2006.01) | |
| *C09D 11/037* | (2014.01) | |
| *G02B 1/04* | (2006.01) | |
| *G02B 5/20* | (2006.01) | |
| *G03F 7/004* | (2006.01) | |
| *G03G 9/09* | (2006.01) | |

(52) U.S. Cl.
CPC ............. *C09B 55/009* (2013.01); *B41M 5/39* (2013.01); *C09D 11/037* (2013.01); *G02B 1/04* (2013.01); *G03F 7/0045* (2013.01); *G03G 9/0906* (2013.01); *G02B 5/20* (2013.01)

(58) Field of Classification Search
CPC ....................................................... B41M 5/39
See application file for complete search history.

(56) References Cited

U.S. PATENT DOCUMENTS

| | | | |
|---|---|---|---|
| 5,079,365 A | 1/1992 | Sens et al. | |
| 5,147,845 A | 9/1992 | Sens et al. | |
| 5,421,834 A | 6/1995 | Etzbach et al. | |
| 5,489,312 A | 2/1996 | Etzbach et al. | |

(Continued)

FOREIGN PATENT DOCUMENTS

| | | |
|---|---|---|
| CN | 104350422 A | 2/2015 |
| CN | 106061748 A | 10/2016 |

(Continued)

OTHER PUBLICATIONS

English machine translation of the description of WO-2013187493-A1 (Year: 2013).*

(Continued)

*Primary Examiner* — Peter L Vajda
*Assistant Examiner* — Boone Alexander Evans
(74) *Attorney, Agent, or Firm* — Venable LLP

(57) ABSTRACT

The azomethine compound provided by this case is a compound showing high chroma and having excellent light resistance.

20 Claims, 1 Drawing Sheet

(56) References Cited

U.S. PATENT DOCUMENTS

| | | |
|---|---|---|
| 5,916,721 A | 6/1999 | Soeda et al. |
| 6,265,345 B1 | 7/2001 | Yoshida et al. |
| 9,146,486 B2 | 9/2015 | Shintou et al. |
| 9,170,513 B2 | 10/2015 | Mori et al. |
| 9,323,168 B2 | 4/2016 | Mori et al. |
| 9,580,576 B2 | 2/2017 | Mori et al. |
| 9,592,695 B2 | 3/2017 | Katsumoto et al. |
| 9,701,146 B2 | 7/2017 | Shirota et al. |
| 9,811,014 B2 | 11/2017 | Mori et al. |
| 10,195,886 B2 | 2/2019 | Santo et al. |
| 2016/0303882 A1* | 10/2016 | Shirota .................. C09D 11/30 |
| 2018/0147875 A1 | 5/2018 | Santo et al. |
| 2020/0339814 A1 | 10/2020 | Shintou et al. |

FOREIGN PATENT DOCUMENTS

| | | | |
|---|---|---|---|
| CN | 107418249 A | 12/2017 | |
| DE | 4217973 A1 | 12/1993 | |
| EP | 0 968 838 A1 | 1/2000 | |
| JP | 6-65519 A | 3/1994 | |
| JP | 10-123759 A | 5/1998 | |
| JP | 2000-006540 A | 1/2000 | |
| JP | 2014-015607 A | 1/2014 | |
| JP | 2016-204651 A | 12/2016 | |
| JP | 2018-089960 A | 6/2018 | |
| WO | WO-2013187493 A1 * | 12/2013 | ............. C09B 23/00 |
| WO | 2020/026855 A1 | 2/2020 | |

OTHER PUBLICATIONS

Non-final Office Action in U.S. Appl. No. 16/925,588 (Feb. 2021).
International Search Report in International Application No. PCT/JP2019/028485 (Sep. 2019).
Extended European Search Report in European Application No. 19844360.8 (May 2022).
First Office Action in Chinese Application No. 201980050753.4 (Dec. 2022).
Final Office Action in U.S. Appl. No. 16/925,588 (Jun. 2021).

* cited by examiner

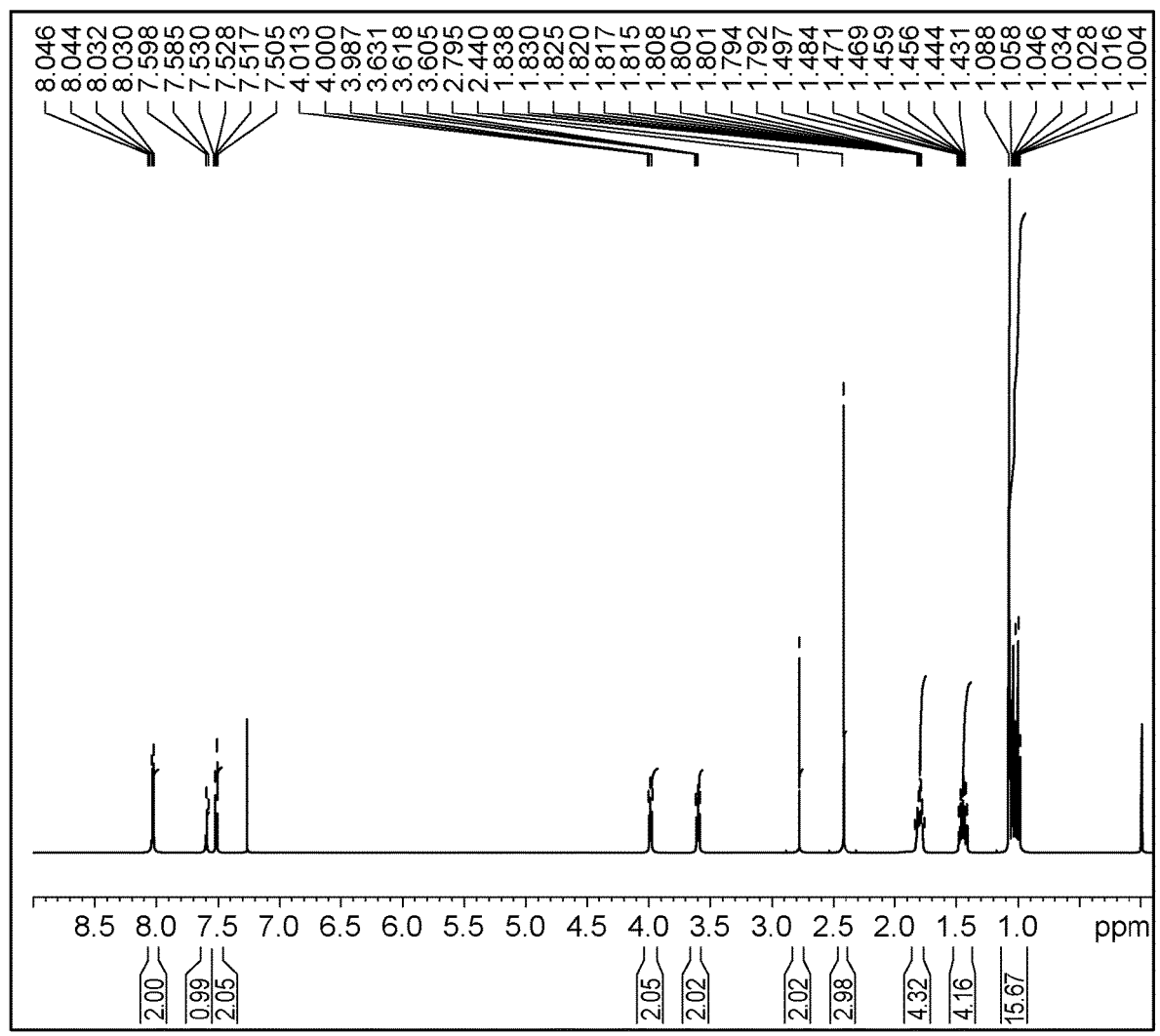

COMPOUND, INK, RESIST COMPOSITION FOR COLOR FILTER, COLOR FILTER, SHEET FOR THERMAL TRANSFER RECORDING, AND TONER

CROSS-REFERENCE TO RELATED APPLICATIONS

This application is a Continuation of International Patent Application No. PCT/JP2019/028485, filed Jul. 19, 2019, which claims the benefit of Japanese Patent Application No. 2018-142389, filed Jul. 30, 2018 and Japanese Patent Application No. 2019-131445, filed Jul. 16, 2019, all of which are hereby incorporated by reference herein in their entirety.

TECHNICAL FIELD

The present invention relates to a compound, an ink containing the compound, a resist composition for a color filter, a sheet for thermal transfer recording, and a toner.

BACKGROUND ART

In color displays using liquid crystals, color filters are used. A color filter is indispensable for color display of a liquid crystal display and is an important component that affects the performance of the liquid crystal display. As known methods for manufacturing color filters, a dyeing method, a printing method, an ink jet method, and a photoresist method are known. Among these methods, the photoresist method is the mainstream because it easily controls the spectral characteristics and color reproducibility and can perform finer patterning with high resolution.

In manufacturing of color filters by the photoresist method, pigments have generally been used as colorants. However, a color filter using a pigment has many problems, such as depolarization action (destroying polarization), a reduction in contrast ratio of color display of a liquid crystal display, a decrease in brightness of the color filter, and a decrease in dispersion stability in an organic solvent or polymer. Accordingly, attention is being paid to a manufacturing method using a dye as the colorant. PTL 1 reports a color filter using an azomethine coloring matter as the colorant.

In addition, in recent years, with the spread of portable color display devices, the demand for easy color printing of taken photographs, processed photographs, and even created documents with these devices is rapidly increasing.

As color printing systems, for example, an electrophotographic system, an ink jet system, a thermal transfer recording system are known. Among these systems, the thermal transfer recording system is excellent as a method that can easily perform printing regardless of the surrounding environment because printing by a dry process is possible, and the printer is small and has excellent portability. In the thermal transfer recording system, the dye contained in a transfer sheet and an ink composition for a transfer sheet affects the transfer recording speed, the image quality of a recorded matter, and storage stability and is therefore a very important material. As the coloring matter to be used in the thermal transfer recording system, an example in which the light resistance is improved by using an azomethine coloring matter has been reported (see PTL 2).

In addition, also in the field of color toners to be used in the electrophotographic system, an example in which a dye is used instead of a pigment usually used as the colorant in order to enhance the color developing properties has been reported. PTL 3 discloses an example of using an azomethine dye as the colorant of a toner.

Furthermore, digital textile printing using an ink jet system or an electrophotographic system is spreading in the market as a method that can provide textile printed products at a low energy and a low cost. In particular, a system of dyeing a synthetic fiber, such as polyester, with a sublimation dye has attracted attention in recent years from the point of simplifying the process and being free from drainage. In this use, since the dye needs to sublimate, phthalocyanine having a large molecular weight cannot be used, and anthraquinone type cyan color is used, which has a problem in the color developing properties.

The azomethine coloring matter described in the above-mentioned literatures has problems of low chroma and tendency of aggregation.

It is an object of the present invention to provide a compound having excellent light resistance while maintaining high chroma. It is also an object of the present invention to provide an ink, a resist composition for a color filter, a color filter, a thermal transfer recording sheet, and a toner having excellent high chroma and high light resistance by using the compound having excellent light resistance while maintaining high chroma.

CITATION LIST

Patent Literature

PTL 1 International Publication No. WO 2013/187493
PTL 2 Japanese Patent Laid-Open No. 2000-006540
PTL 3 German Patent Application Publication No. DE 4217973

SUMMARY OF INVENTION

The present invention relates to a compound represented by the following Formula (1):

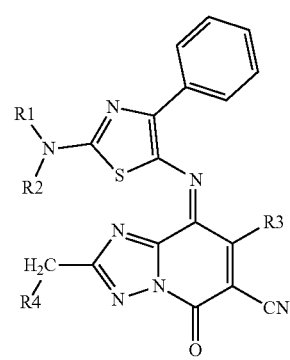

Formula (1)

[in Formula (1), R1 and R2 each independently represent a linear alkyl group having 1 to 12 carbon atoms or a branched alkyl group having 3 to 12 carbon atoms; R3 represents an alkyl group having 1 to 4 carbon atoms; and R4 represents a functional group selected from the group consisting of a t-butyl group, an iso-propyl group, a phenyl group, and a benzyl group].

The present invention also relates to an ink containing a medium and the above compound.

The present invention also relates to a resist composition for a color filter containing the above compound.

The present invention also relates to a color filter containing the above compound.

The present invention also relates to a thermal transfer recording sheet including a substrate and a color material layer formed on the substrate, wherein the color material layer contains the above compound.

The present invention also relates to a toner containing a binder resin and a colorant, wherein the colorant contains the above compound.

Further features of the present invention will become apparent from the following description of exemplary embodiments with reference to the attached drawings.

BRIEF DESCRIPTION OF DRAWING

FIGURE is a diagram showing a $^1$H-NMR spectrum of compound (1-1) of the present invention.

DESCRIPTION OF EMBODIMENTS

Embodiments of the present invention will now be described in detail, but the present invention is not limited to them.

The present inventors have diligently studied to solve the above problems and, as a result, have found that the following compound is excellent in the points of high chroma and high light resistance.

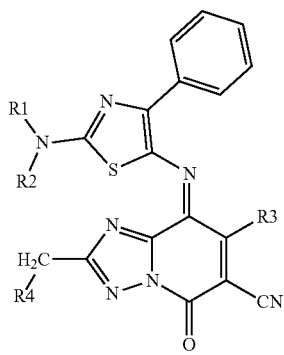

Formula (1)

[In Formula (1), R1 and R2 each independently represent a linear alkyl group having 1 to 12 carbon atoms or a branched alkyl group having 3 to 12 carbon atoms; R3 represents an alkyl group having 1 to 4 carbon atoms; and R4 represents a functional group selected from the group consisting of a t-butyl group, an iso-propyl group, a phenyl group, and a benzyl group.]

As described in known technologies, when the substituent at the 2-position of [1,2,4]triazolo[1,5-a]pyridine ring has a structure with a branch, such as a 2-ethylhexyl group, repulsion with the alkylamino group of the thiazole ring occurs by three-dimensional interaction. In contrast, in the compound of the present invention, the substituent at the 2-position of [1,2,4]triazolo[1,5-a]pyridine ring includes a branched alkyl group, a phenyl group, or a benzyl group via one methylene group. Accordingly, it is inferred that since the three-dimensional interaction of the thiazole ring with the alkylamino group is relieved, a compound having excellent light resistance while maintaining high chroma is obtained.

In addition, it has been found that it is possible to obtain an ink, a resist composition for a color filter, a thermal transfer recording sheet, and a toner having excellent light resistance while maintaining high chroma by using the compound represented by Formula (1) which has excellent light resistance while maintaining high chroma.

First of all, the compound represented by the Formula (1) will be described.

In Formula (1), the linear alkyl group having 1 to 12 carbon atoms, the branched alkyl group having 3 to 12 carbon atoms, and the cyclic alkyl group having 3 to 12 carbon atoms as R1 and R2 are not particularly limited, and examples thereof include a methyl group, an ethyl group, an n-propyl group, an iso-propyl group, an n-butyl group, a sec-butyl group, a tert-butyl group, an n-hexyl group, an n-heptyl group, an n-octyl group, an n-nonyl group, an n-decyl group, an n-undecyl group, an n-dodecyl group, a 2-ethylhexyl group, and a cyclohexyl group.

Among these groups, from the viewpoint that a compound has excellent light resistance while maintaining high chroma, an alkyl group having 8 carbon atoms is preferable, and, in particular, a branched alkyl group, such as a 2-ethylhexyl group, is more preferable.

In Formula (1), the linear alkyl group having 1 to 4 carbon atoms as R3 is not particular limited, and examples thereof include a methyl group, an ethyl group, an n-propyl group, and an n-butyl group. In addition, examples of the branched alkyl group having 3 or 4 carbon atoms include an iso-propyl group, a sec-butyl group, and a tert-butyl group. Among these groups, a methyl group, an ethyl group, and an n-butyl group are preferable.

In Formula (1), R4 represents a functional group selected from the group consisting of a t-butyl group, an iso-propyl group, a phenyl group, and a benzyl group. Among these groups, a t-butyl group and a phenyl group are preferable.

Secondly, a method for manufacturing the compound represented by Formula (1) will be described. The compound of the present invention can be synthesized with reference to the known method described in a patent literature (Japanese Patent Laid-Open No. 08-245896). An example of the method for manufacturing the compound of the present invention will now be described, but the manufacturing method is not limited thereto.

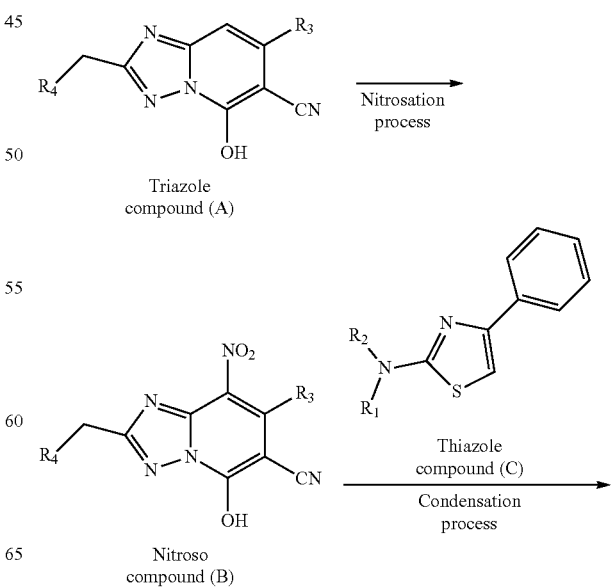

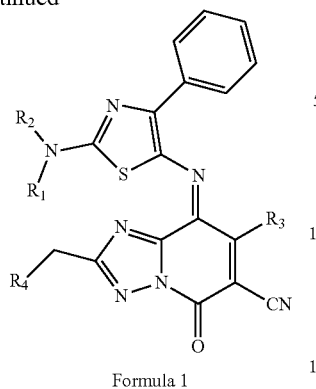

Formula 1

Incidentally, R1 to R4 in each compound in the above reaction formulae are synonymous with those described above. In addition, the compound represented by Formula (1) has cis-trans isomers, and every isomers are within the scope of the present invention. The compound represented by Formula (1) may be a mixture thereof.

The compound of the present invention represented by Formula (1) can be manufactured by inducing a triazole compound (A) to a nitroso compound by a nitrosation process and then condensing the nitroso compound with a thiazole compound (C) by a condensation reaction.

The condensation process for obtaining the compound of the present invention represented by Formula (1) will be described.

The compound of the present invention can be manufactured by inducing a triazole compound (A) to a nitroso compound by a nitrosation process and then condensing the nitroso compound with a thiazole compound (C) by a condensation reaction.

Preferred examples of the triazole compound (A) are shown as the following (A-1) to (A-11), but the present invention is not limited thereto.

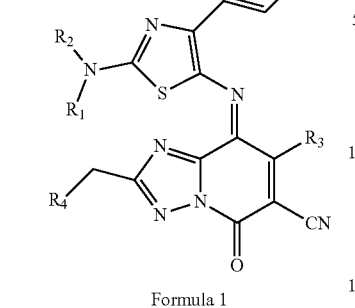
(A-1)

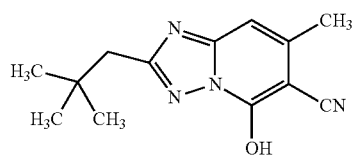
(A-2)

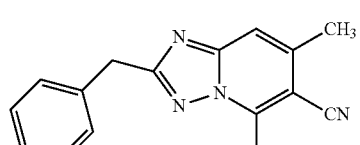
(A-3)

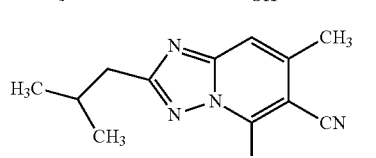
(A-4)

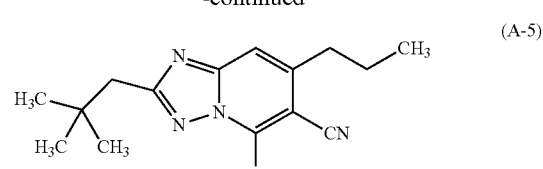
(A-5)

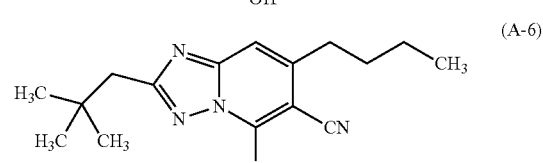
(A-6)

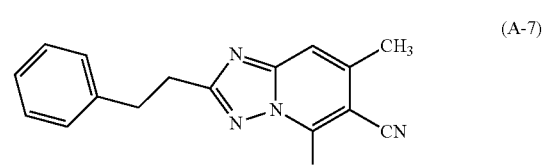
(A-7)

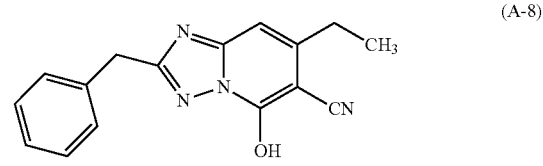
(A-8)

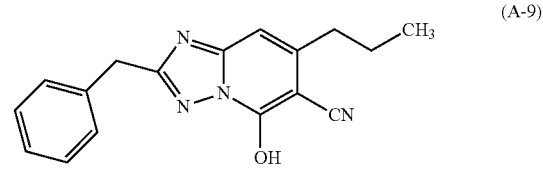
(A-9)

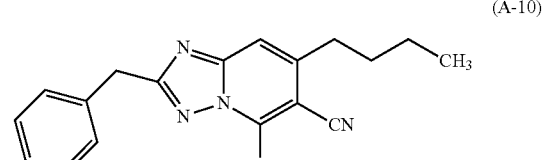
(A-10)

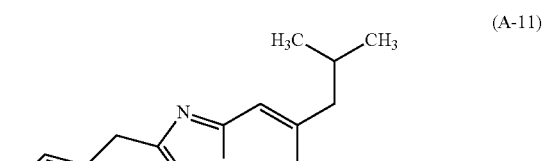
(A-11)

Preferred examples of the thiazole compound (C) are shown as the following (C-1) to (C-4), but the present invention is not limited thereto.

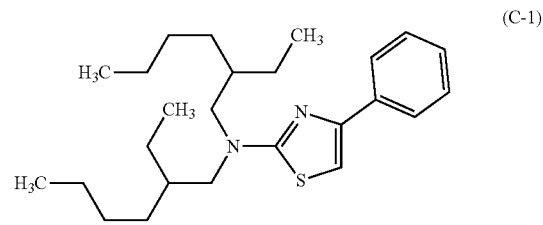
(C-1)

(C-2)

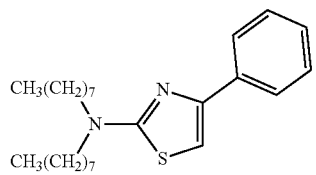

(C-3)

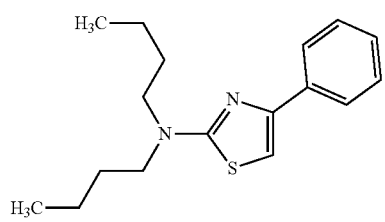

(C-4)

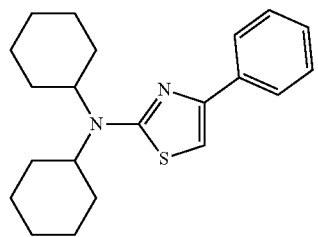

The condensation reaction can be a solvent-free reaction but is preferably performed in the presence of a solvent. The solvent is not particularly limited as long as the reaction is not inhibited, and examples thereof include chloroform, dichloromethane, N,N-dimethylformamide, toluene, xylene, tetrahydrofuran, dioxane, acetonitrile, ethyl acetate, methanol, ethanol, and isopropanol. These solvents may be used alone or as a mixture of two or more thereof. The mixing ratio when used as a mixture can be arbitrarily determined. The amount of the reaction solvent to be used is preferably 0.1 to 1,000 mass % and more preferably 1.0 to 150 mass % with respect to triazole compound (A).

The reaction temperature in the condensation reaction is preferably within a range of −80° C. to 250° C. and more preferably −20° C. to 150° C. The condensation reaction usually ends within 24 hours.

In addition, in the condensation reaction, in order to enhance the reaction, an acid or a base is preferably used. Specifically, examples of the acid include inorganic acids, such as hydrochloric acid, sulfuric acid, and phosphoric acid; and organic acids, such as p-toluenesulfonic acid, formic acid, acetic acid, propionic acid, and trifluoroacetic acid. In addition, weak acidic salts, such as ammonium formate and ammonium acetate, can also be used similar to the above acids. Among these acids, p-toluenesulfonic acid, ammonium formate, and ammonium acetate are preferable.

The amount of the acid to be used is preferably 0.01 to 20 mass % and more preferably 0.1 to 5 mass % with respect to the thiazole compound (A).

In addition, specifically, examples of the base include organic bases, such as pyridine, 2-methylpyridine, piperidine, diethylamine, diisopropylamine, triethylamine, phenylethylamine, isopropylethylamine, methylaniline, 1,4-diazabicyclo[2.2.2]octane (DABCO), tetrabutylammonium hydroxide, and 1,8-diazabicyclo[5.4.0]undecene (DBU); organic metals, such as n-butyllithium and tert-butylmagnesium chloride; inorganic bases, such as sodium borohydride, metallic sodium, potassium hydride, and calcium oxide; and metal alkoxides, such as potassium tert-butoxide, sodium tert-butoxide, and sodium ethoxide. Among these bases, triethylamine and piperidine are preferable, and triethylamine is more preferable. The amount of the base to be used is preferably 0.1 to 20 mass % and more preferably 0.2 to 5 mass % with respect to the thiazole compound (A). In addition, as in the bases above, weak basic salts, such as potassium acetate, can also be used similar to the above bases.

The compound of the present invention represented by Formula (1) can be obtained with high purity by performing, after completion of the condensation reaction, post-treatment in accordance with a post-treatment method that is usually used in an organic synthetic reaction and performing purification, such as liquid separation operation, recrystallization, reprecipitation, and column chromatography, as needed.

Preferred examples of the compound of the present invention represented by Formula (1) are shown as the following (1-1) to (1-15), but the present invention is not limited thereto.

(1-1)

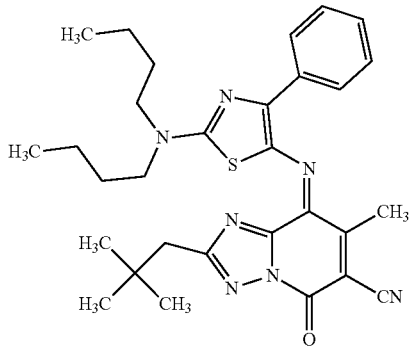

(1-2)

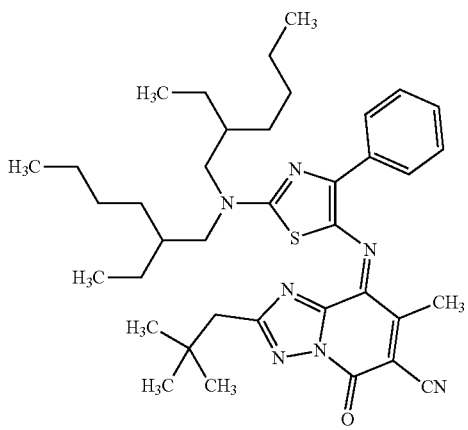

(1-3)
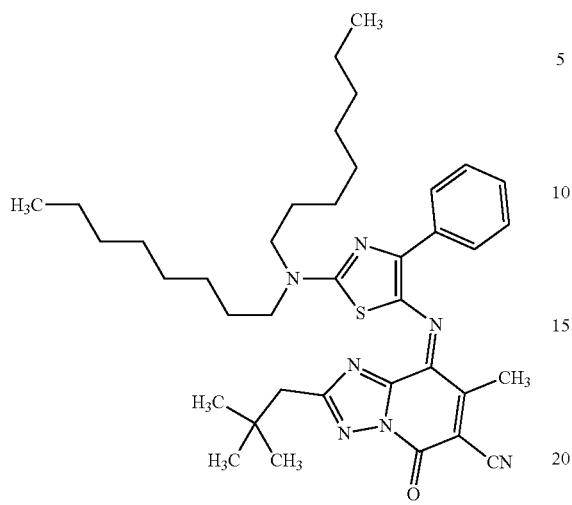
(1-4)
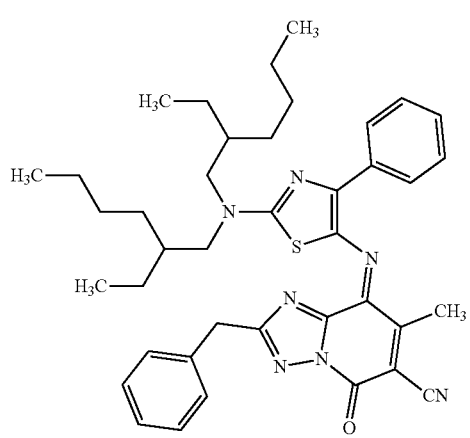
(1-5)
(1-6)
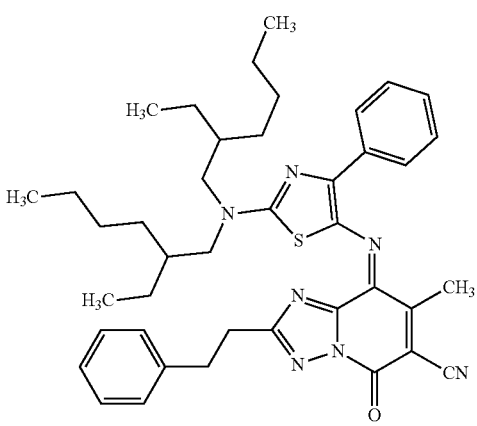
(1-7)
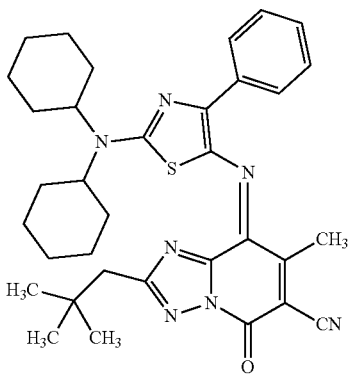
(1-8)
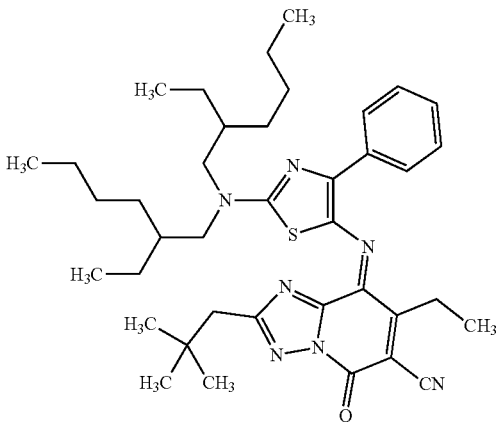

-continued
(1-9)
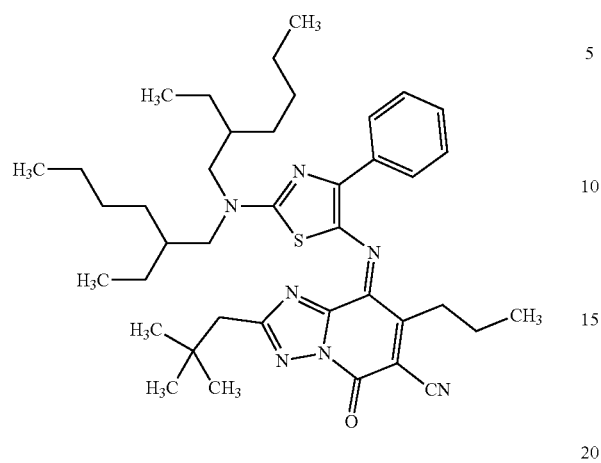
(1-10)
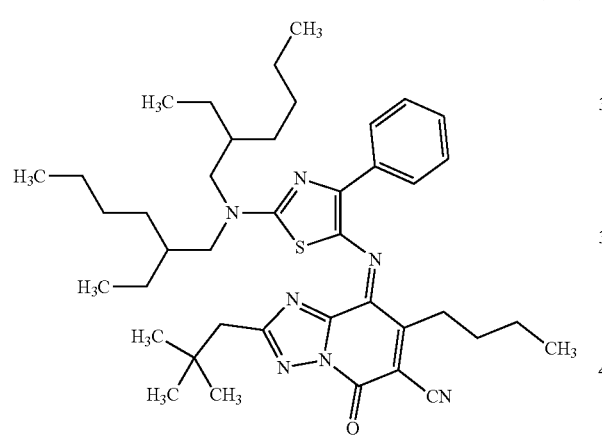
(1-11)
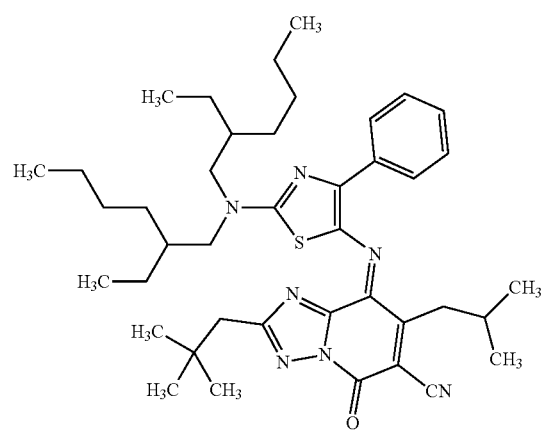
-continued
(1-12)
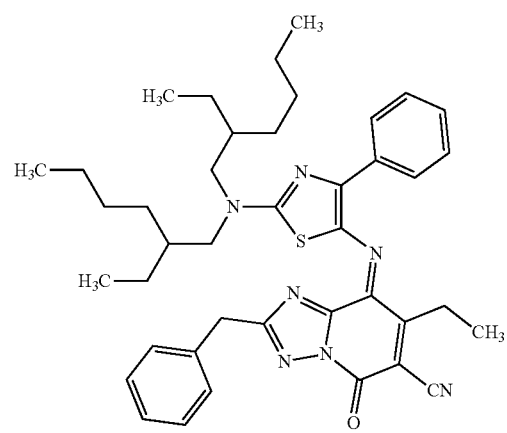
(1-13)
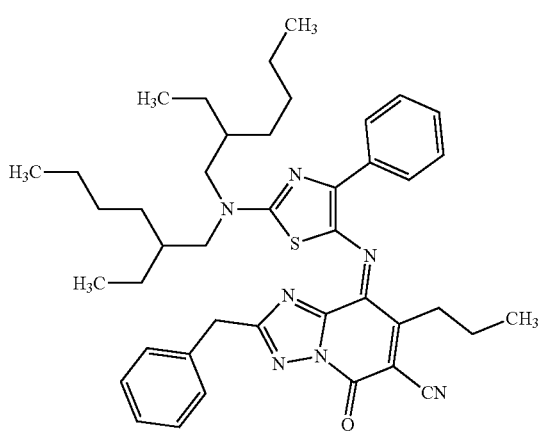
(1-14)
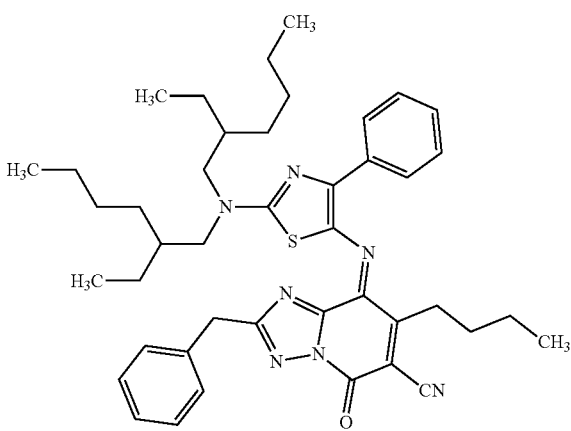

-continued (1-15)

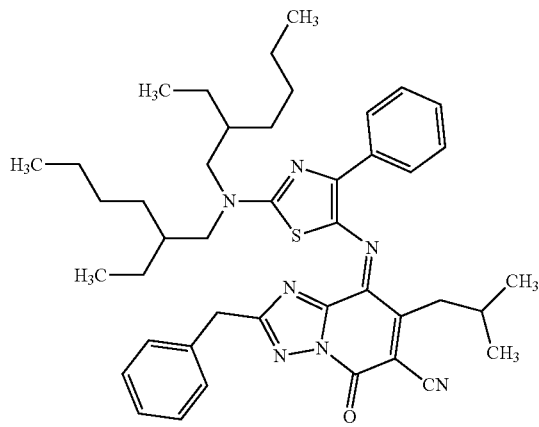

The compounds represented by the Formula (1) may be used alone or in combination of two or more thereof for adjusting the color tone, etc. according to the intended use. Furthermore, the compound can also be used in combination with a known pigment or dye. In such a case, two or more known pigments or dyes may be used in combination.

An ink, a resist composition for a color filter, a color filter, a thermal transfer recording sheet, and a toner using the compound represented by the Formula (1) will now be described one by one.

Ink

An ink according to the present invention will first be described. The compound represented by Formula (1) having excellent light resistance while maintaining high chroma is suitable as a colorant for an ink. The ink of the present invention contains a medium and the compound represented by Formula (1) as a colorant. The compound is present in a state of being dissolved or dispersed in the medium. In the ink of the present invention, the components other than the compound represented by Formula (1) can be appropriately selected according to the use of the ink. In addition, for example, additives may be appropriately added within a range of not inhibiting the characteristics in each use.

The ink of the present invention is also suitable as an ink for transfer sheet for a thermal transfer recording system printer, an ink for printing, a paint, an ink for writing instruments, or an ink for textile printing.

When the ink of the present invention is used as an ink for textile printing, the fabric on which textile printing can be performed is not particularly limited as long as it can be dyed, and examples thereof include fabrics made of fibers containing polyester, acetate, or triacetate. The fabric may be in any form such as a woven fabric, a knitted fabric, and a non-woven fabric. In addition, a fabric made of cotton, silk, linen, polyurethane, acryl, nylon, wool, or rayon fibers or a fabric made of a combination of two or more of these fibers can also be used.

The thickness of thread constituting the fabric is preferably within a range of 10 to 100 deniers. The thickness of the fiber constituting the thread is not particularly limited and is preferably 1 denier or less.

The ink of the present invention can be prepared as follows.

The compound of the present invention and, for example, another colorant, an emulsifier, and a resin as needed are gradually added to a medium with stirring to sufficiently blend with the medium. Furthermore, the dissolution or fine dispersion is stabilized by applying a mechanical shear force with a disperser. The ink of the present invention can thereby be obtained.

Medium

In the present invention, the term "medium" means water or an organic solvent. When an organic solvent is used as the medium, the type of the organic solvent is selected according to the purpose and use of the ink and is not particularly limited. Examples of the organic solvent include alcohols, such as methanol, ethanol, modified ethanol, isopropanol, n-butanol, isobutanol, tert-butanol, sec-butanol, 2-methyl-2-butanol, 3-pentanol, octanol, benzyl alcohol, and cyclohexanol; glycols, such as methyl cellosolve, ethyl cellosolve, diethylene glycol, and diethylene glycol monobutyl ether; ketones, such as acetone, methyl ethyl ketone, and methyl isobutyl ketone; esters, such as ethyl acetate, butyl acetate, ethyl propionate, and cellosolve acetate; aliphatic hydrocarbons, such as hexane, octane, petroleum ether, and cyclohexane; aromatic hydrocarbons, such as benzene, toluene, and xylene; halogenated hydrocarbons, such as carbon tetrachloride, trichloroethylene, and tetrabromoethane; ethers, such as diethyl ether, dimethyl glycol, trioxane, and tetrahydrofuran; acetals, such as methylal and diethyl acetal; organic acids, such as formic acid, acetic acid, and propionic acid; and sulfur- or nitrogen-containing organic compounds, such as nitrobenzene, dimethylamine, monoethanolamine, pyridine, dimethylsulfoxide, and dimethylformamide.

In addition, as the organic solvent, a polymerizable monomer can also be used. As the polymerizable monomer, an addition polymerizable monomer and a condensation polymerizable monomer are mentioned, and an addition polymerizable monomer is preferable. Specifically, examples of the polymerizable monomer include styrene monomers, such as styrene, α-methylstyrene, α-ethylstyrene, o-methylstyrene, m-methylstyrene, p-methylstyrene, o-ethylstyrene, m-ethylstyrene, and p-ethylstyrene; acrylate monomers, such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and amide acrylate; methacrylate monomers, such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and amide methacrylate; olefin monomers, such as ethylene, propylene, butylene, butadiene, isoprene, isobutylene, and cyclohexene; halogenated vinyl monomers, such as vinyl chloride, vinylidene chloride, vinyl bromide, and vinyl iodide; vinyl ester monomers, such as vinyl acetate, vinyl propionate, and vinyl benzoate; vinyl ether monomers, such as vinyl methyl ether, vinyl ethyl ether, and vinyl isobutyl ether; and vinyl ketone monomers, such as vinyl methyl ketone, vinyl hexyl ketone, and methyl isopropenyl ketone. These monomers may be used alone or in combination of two or more thereof as needed.

Dispersant

When water is used as the medium of the ink, in order to obtain good dispersion stability of the colorant, a dispersant may be added as needed. The dispersant is not particularly limited, and examples thereof include a cationic surfactant, an anionic surfactant, and a nonionic surfactant.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soaps, such as sodium stearate and sodium dodecanoate, sodium dodecyl sulfate, sodium dodecyl benzene sulfate, sodium lauryl sulfate, naphthalene, and a formalin condensate of β-naphthalenesulfonic acid.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

Colorant

As the colorant constituting the ink, the compound represented by Formula (1) is used, and the compound used may be one compound or a combination of two or more compounds. In addition, another colorant, such as a known dye, may also be used within a range of not inhibiting the solubility or dispersibility of the compound in the medium. The additional colorant that can be used in combination is not particularly limited, and examples thereof include a condensed azo compound, an azo metal complex, and a methine compound.

The content of the colorant is preferably 1.0 to 30 parts by mass based on 1,000 parts by mass of the medium and more preferably 2.0 to 20 parts by mass and particularly preferably 3.0 to 15 pats by mass. When the content is within the above range, sufficient tinting strength can be obtained, and also the colorant is well dispersed.

Resin

The ink may further contain a resin. The type of the resin in determined according to the purpose and use of the ink and is not particularly limited. Examples of the resin include a styrene polymer, an acrylic acid polymer, a methacrylic acid polymer, a polyester resin, a polyvinyl ether resin, a polyvinyl methyl ether resin, a polyvinyl alcohol resin, a polyvinyl butyral resin, a polyurethane resin, and a polypeptide resin. These resins may be used alone or in combination of two or more thereof as needed.

Although the disperser is not particularly limited, a rotation shearing type homogenizer, a media type disperser such as a ball mill, a sand mill, or an attritor, or a high-pressure counter-collision type disperser can be used.

As described above, since the ink of the present invention contains the compound represented by Formula (1), it is possible to provide an ink showing cyan color having high chroma, high light resistance, and excellent storage stability.

Thermal Transfer Recording Sheet

Then, the thermal transfer recording sheet according to the present invention will be described. The compound of the present invention having excellent light resistance while maintaining high chroma can be suitably used in the thermal transfer recording sheet.

The thermal transfer recording sheet according to the present invention includes a substrate and a color material layer that is a film formed from a composition containing the compound of the present invention on the substrate. The color material layer at least includes a yellow layer containing a yellow dye, a magenta layer containing a magenta dye, and a cyan layer containing a cyan dye.

In a thermal transfer recording method, an image is formed by heating a thermal transfer recording sheet with a heating means, such as a thermal head, in a state that the color material layer of the thermal transfer recording sheet and an image-receiving sheet provided with a color material-receiving layer on a surface are stacked, to transfer the color material in the sheet to the image-receiving sheet.

The color material layer is basically formed by applying a coating liquid containing the above-described ink of the present invention and a binder resin to a substrate sheet and drying it. The details will be further described below.

A color material including the compound represented by Formula (1), a binder resin, and a surfactant and wax as needed are gradually added to a medium with stirring to sufficiently blend with the medium. Subsequently, a mechanical shear force is applied to the mixture with a disperser to stably dissolve or finely disperse the composition in the medium to prepare an ink. The ink is applied to a base film as the substrate and dried to form a color material layer. Furthermore, as needed, a transfer protection layer, a heat-resistant lubricant layer, and so on are formed to provide a thermal transfer recording sheet of the present invention. Incidentally, the thermal transfer recording sheet of the present invention is not limited to the thermal transfer recording sheet produced by the above-described manufacturing method. Each component used in the color material layer will now be described in detail.

Color Material (i) Cyan Dye (Compounds of Formulae (1) and (2))

As the color material that can be used in the thermal transfer recording sheet, a compound represented by Formula (1) is used, and the compound used may be one compound or a combination of two or more compounds. Furthermore, it is preferable to include the compound represented by Formula (2) as the cyan dye.

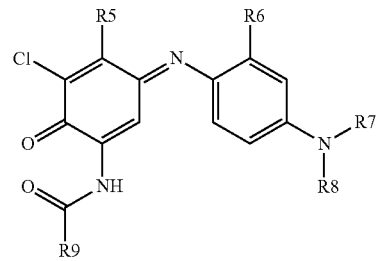

Formula (2)

In Formula (2), R5 to R9 each independently represent an alkyl group or an aryl group.

In Formula (2), the alkyl group and the aryl group represented by R5 to R9 are not particularly limited.

In Formula (2), the alkyl groups represented by R5 to R9 are preferably linear or branched alkyl groups having 1 to 4 carbon atoms (e.g., a methyl group, an ethyl group, an n-butyl group, and a t-butyl group). Furthermore, in these alkyl groups, from the viewpoint of obtaining an image having excellent light resistance while maintaining high chroma, alkyl groups having 1 or 2 carbon atoms (methyl group and ethyl group) are more preferable.

In Formula (2), examples of the aryl group represented by R5 to R9 include a phenyl group and a naphthyl group. In particular, a phenyl group is preferable because images having excellent light resistance are easily obtained while maintaining high chroma.

As examples of the compound represented by Formula (2), compounds (2-1) to (2-7) are shown below, but the compound is not limited to the following compounds.

Compound (2-1)
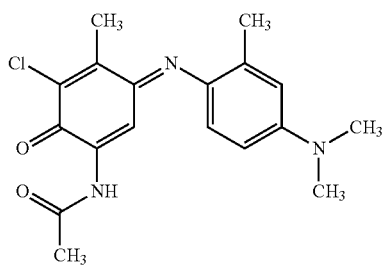

Compound (2-2)
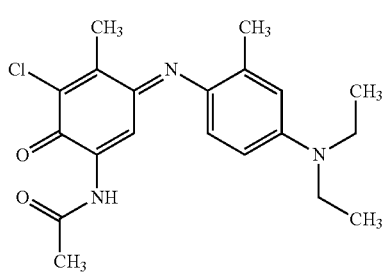

Compound (2-3)
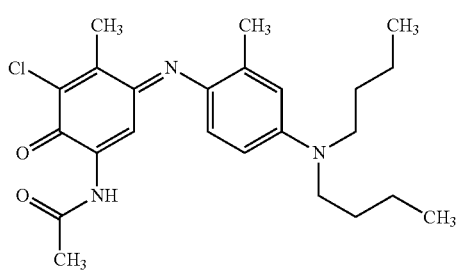

Compound (2-4)
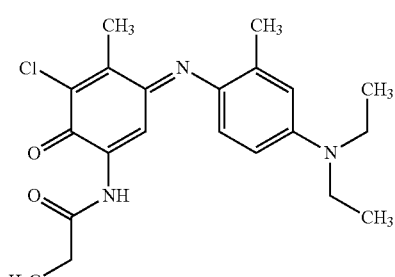

Compound (2-5)
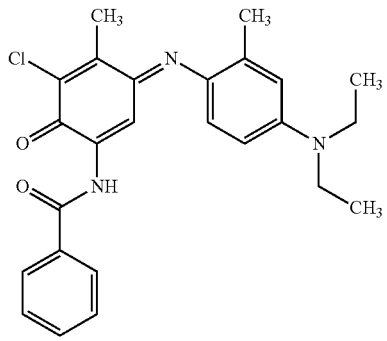

Compound (2-6)
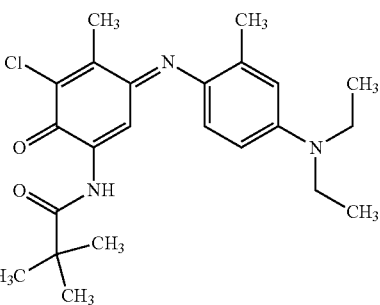

Compound (2-7)
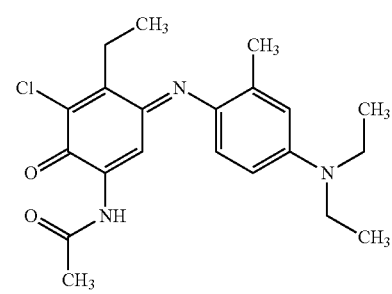

Among the compounds of Formula (2), it is preferable to use at least one of the compounds (2-1) to (2-3) as the cyan dye. In addition, it is more preferable to use the compound (2-2) as the compound of Formula (2) because images having excellent light resistance are easily obtained while maintaining high chroma.

In addition, a known color material that is used in the cyan layer for thermal transfer can also be used in combination. Regarding the color material used in combination, it is necessary to consider, for example, the hue, printing sensitivity, light resistance, storage stability, and solubility in a binder resin.

(ii) Yellow Dye (Compounds of Formulae (3) to (5))

The yellow layer of the thermal transfer recording sheet contains one or more compounds selected from the group of compounds represented by the following Formulae (3) to (5) as the yellow dye. That is, as the yellow dye, these compounds may be used alone or in combination of two or more thereof.

(ii-1) Compound of Formula (3)

Next, the compound (yellow dye) represented by Formula (3) will be described.

Formula (3)
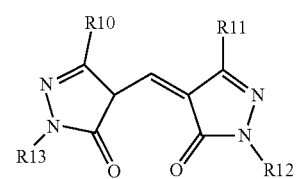

In the Formula (3), R10 to R13 each independently represent an alkyl group or an aryl group optionally having a substituent.

In Formula (3), the alkyl group represented by R10 to R13 is not particularly limited as long as it is an alkyl group. As the alkyl group, for example, linear, branched, or cyclic primary to tertiary alkyl groups having 1 to 20 carbon atoms are mentioned.

More specifically, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, and a 2-ethylhexyl group are mentioned.

Among these alkyl groups, an alkyl group having 1 to 4 carbon atoms is preferable because images having excellent light resistance are easily obtained while maintaining high chroma.

In the Formula (3), the aryl group optionally having a substituent represented by R10 to R13 is not particularly limited as long as it is a substituted or unsubstituted aryl group. As the substituent, for example, an alkyl group is mentioned. The total number of carbon atoms of the aryl group is preferably, for example, 6 to 10 including the number of carbon atoms of the substituent.

Examples of the aryl group optionally having a substituent include a phenyl group, a tolyl group (a 2-methylphenyl group, a 3-methylphenyl group, or a 4-methylphenyl group), and a naphthyl group. Among these aryl groups, a phenyl group is preferable because images having excellent light resistance are easily obtained while maintaining high chroma.

As examples of the compound represented by Formula (3), compounds (3-1) to (3-8) are shown below, but the compound is not limited to the following compounds.

Compound (3-1)

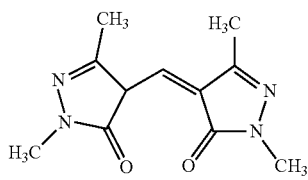

Compound (3-2)

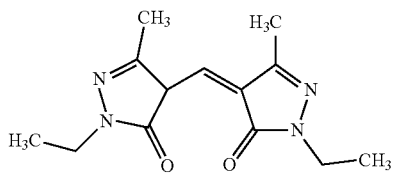

Compound (3-3)

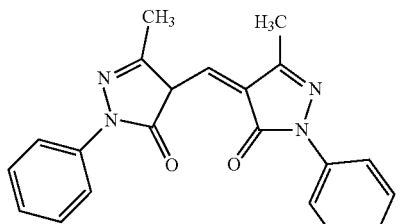

Compound (3-4)

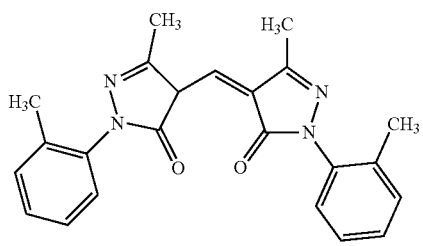

Compound (3-5)

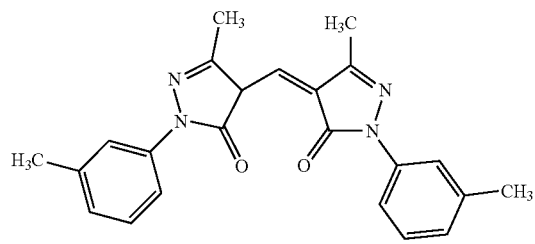

Compound (3-6)

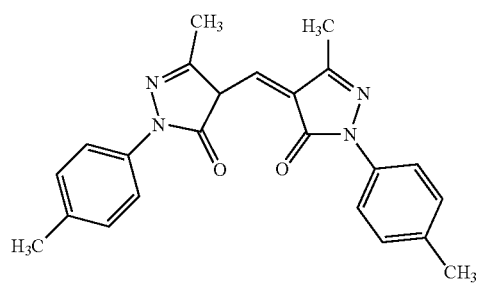

Compound (3-7)

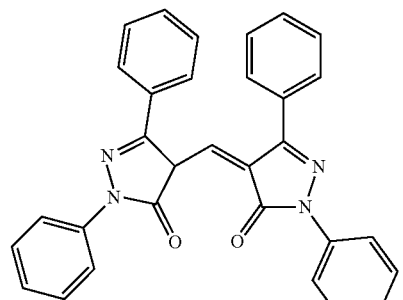

Compound (3-8)

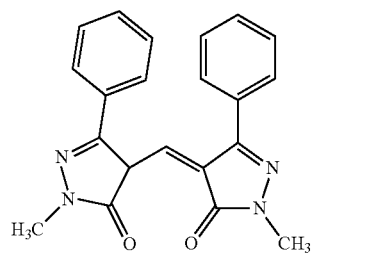

Among the compounds of Formula (3), it is preferable to use at least one of the compounds (3-2) to (3-5) as the yellow dye. In addition, it is more preferable to use compound (3-2) as the compound of Formula (3) because images having excellent light resistance are easily obtained while maintaining high chroma.

(ii-2) Compound of Formula (4)

Then, the compound (yellow dye) represented by Formula (4) will be described.

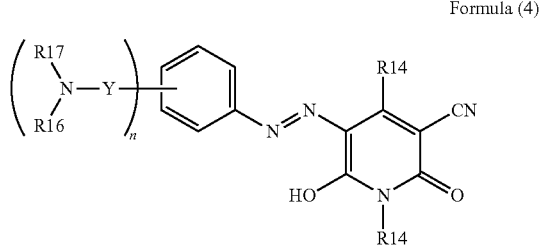

Formula (4)

In the Formula (4), R14 represents an alkyl group, an aryl group optionally having a substituent, or an amino group optionally having a substituent. R15 represents a hydrogen atom, an alkyl group, an aryl group optionally having a substituent, or —N(—R$^a$)R$^b$, where R$^a$ and R$^b$ each independently represent a hydrogen atom, an alkyl group, or an acyl group. In addition, R$^a$ and R$^b$ may bind to each other to form a ring. R16 represents an alkyl group. R17 represents a hydrogen atom or an alkyl group. Y represents a carbonyl group (—C(=O)—) or a sulfonyl group (—S(=O)$_2$—). n represents an integer of 1 to 3.

In Formula (4), the alkyl group represented by R14 is not particularly limited as long as it is an alkyl group. As the alkyl group, for example, linear or branched alkyl groups having 1 to 4 carbon atoms, such as a methyl group, an ethyl group, a propyl group, and a butyl group, are mentioned.

In Formula (4), the aryl group optionally having a substituent represented by R14 is not particularly limited as long as it is a substituted or unsubstituted aryl group. As the substituent, for example, alkyl groups, such as a methyl group, are mentioned. The number of carbon atoms of the aryl group is preferably, for example, 6 to 12 including the number of carbon atoms of the substituent.

Examples of the aryl group optionally having a substituent include a phenyl group and a tolyl group (2-methylphenyl group, 3-methylphenyl group, or 4-methylphenyl group).

In Formula (4), the amino group optionally having a substituent represented by R14 is not particularly limited. Examples of the substituent include alkyl groups, such as a methyl group and an ethyl group.

Examples of the amino group optionally having a substituent include a monomethylamino group, a dimethylamino group, and a diethylamino group.

Among these groups, R14 is preferably an alkyl group because images having excellent light resistance are easily obtained while maintaining high chroma. Furthermore, from the same viewpoint, R14 is more preferably a methyl group.

In Formula (4), the alkyl group represented by R15 is not particularly limited as long as it is an alkyl group. As the alkyl group, for example, linear, branched, or cyclic primary to tertiary alkyl groups having 1 to 20 carbon atoms are mentioned.

More specifically, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group are mentioned. Among these alkyl groups, a methyl group, an ethyl group, an n-propyl group, an iso-propyl group, an n-butyl group, and a 2-ethylhexyl group are preferable because images having excellent light resistance are easily obtained while maintaining high chroma. Furthermore, from the same viewpoint, in particular, an ethyl group and an n-propyl group are more preferable.

In Formula (4), the aryl group optionally having a substituent represented by R15 is not particularly limited as long as it is a substituted or unsubstituted aryl group. As the aryl group, for example, those mentioned as R14 of Formula (4) can be similarly mentioned.

In Formula (4), when R15 represents —N(—R$^a$) R$^b$, the alkyl group represented by R$^a$ or R$^b$ is not particularly limited as long as it is an alkyl group. As the alkyl group, for example, those mentioned as R15 of Formula (4) can be similarly mentioned.

In Formula (4), when R15 represents —N(—R$^a$)R$^b$, the acyl group represented by R$^a$ or R$^b$ is not particularly limited as long as it is an acyl group. As the acyl group, for example, alkylcarbonyl groups, such as an acetyl group and an ethylhexynoyl group; and arylcarbonyl groups, such as a benzoyl group, are mentioned.

In Formula (4), when R15 represents —N(—R$^a$)R$^b$, the ring (cyclic structure) formed by binding of R$^a$ and R$^b$ to each other can be appropriately selected from the viewpoint of easily obtaining an image having excellent light resistance while maintaining high chroma and is not particularly limited as long as it is a cyclic structure. As the cyclic structure, for example, pyrrolidine ring, a piperidine ring, an azepane ring, and an azocane ring are mentioned.

Incidentally, among these examples, it is preferable that at least one of R$^a$ and R$^b$ is an alkyl group because images having excellent light resistance are easily obtained while maintaining high chroma. Furthermore, from the same viewpoint, it is more preferable that at least one of R$^a$ and R$^b$ is a methyl group.

In Formula (4), the alkyl group represented by R16 or R17 is not particularly limited as long as it is an alkyl group. As the alkyl group, for example, those mentioned as R15 of Formula (4) can be similarly mentioned.

In addition, among these alkyl groups, R16 and R17 preferably each independently represent the following groups because images having excellent light resistance are easily obtained while maintaining high chroma. That is, an ethyl group, an n-butyl group, a sec-butyl group, a dodecyl group, a cyclohexyl group, a methylcyclohexyl group, a 2-ethylpropyl group, and a 2-ethylhexyl group are preferable, and an n-butyl group and a 2-ethylhexyl group are more preferable. In addition, R16 and R17 preferably represent the same alkyl groups because images having excellent light resistance are easily obtained while maintaining high chroma.

In Formula (4), although Y can represent a carbonyl group or a sulfonyl group, Y preferably represents a carbonyl group because images having excellent light resistance are easily obtained while maintaining high chroma.

In Formula (4), although n represents an integer of 1 to 3 (an integer of 1 or more and 3 or less), n preferably represents 1 because images having excellent light resistance are easily obtained while maintaining high chroma.

Incidentally, although the azo form is shown in Formula (4), the tautomer thereof, the hydrazone form, is also within the scope of the present invention.

In addition, in Formula (4), the bonding site of the R16(R17-)N—Y— group to the phenyl group is not particularly limited and can be appropriately set.

As examples of the compound represented by Formula (4), compounds (4-1) to (4-5) are shown below, but the compound is not limited to the following compounds.

Compound (4-1)

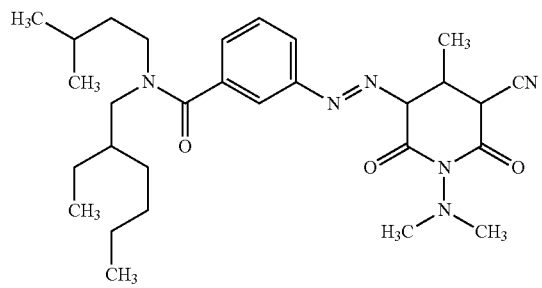

Compound (4-2)

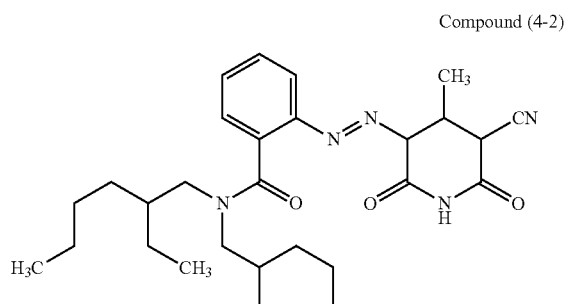

Compound (4-3)

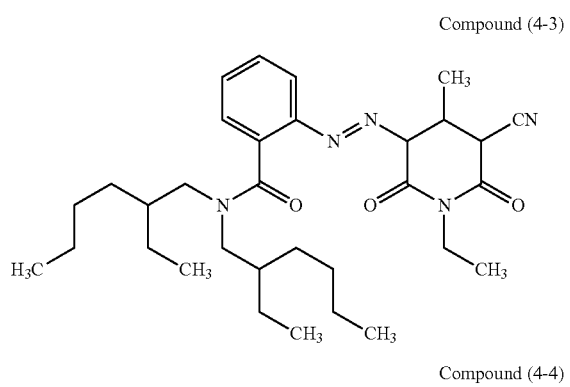

Compound (4-4)

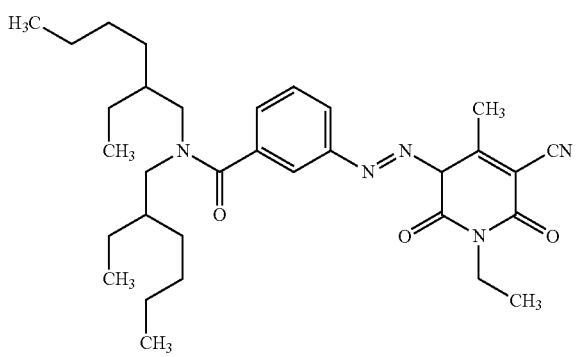

Compound (4-5)

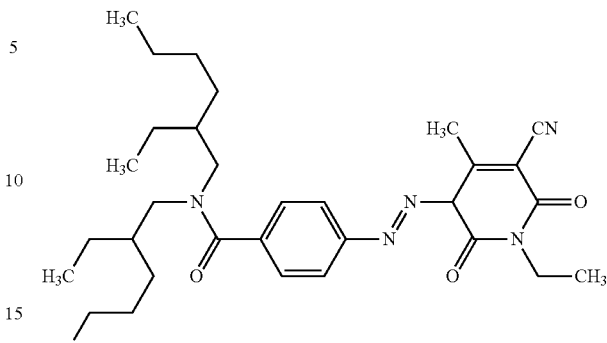

Compound (4-5)

As the yellow dye, among the compounds of Formula (4), at least one of the compounds (4-3), (4-4), and (4-5) is preferably used because images having excellent light resistance are easily obtained while maintaining high chroma.

(ii-3) Compound of Formula (5)

Next, the compound (yellow dye) represented by Formula (5) will be described.

Formula (5)

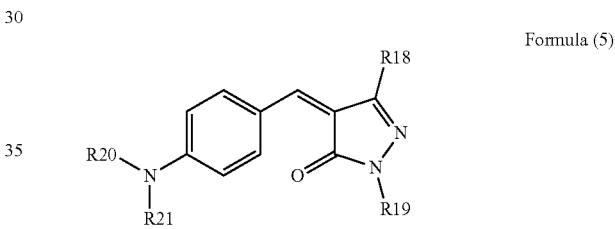

[In Formula (5), R18 represents an alkyl group, an aryl group, or an alkoxy group; R19 represents an alkyl group or an aryl group; and R20 and R21 each independently represent an alkyl group.]

In Formula (5), the alkyl group represented by R18 to R20 are not particularly limited. The alkyl group is particularly preferably an alkyl group having 1 to 4 carbon atoms, i.e., a methyl group, an ethyl group, an n-propyl group, an iso-propyl group, or an n-butyl group, because images having excellent light resistance are easily obtained while maintaining high chroma.

In Formula (5), the aryl group represented by R18 or R19 is not particularly limited. As the aryl group, for example, those mentioned as R14 of Formula (4) can be similarly mentioned.

The alkoxy group represented by R18 is not particularly limited. The alkoxy group is particularly preferably a methoxy group, an ethoxy group, or a propyl group because images having excellent light resistance are easily obtained while maintaining high chroma.

As examples of the compound represented by Formula (5), compounds (5-1) to (5-5) are shown below, but the compound is not limited to the following compounds.

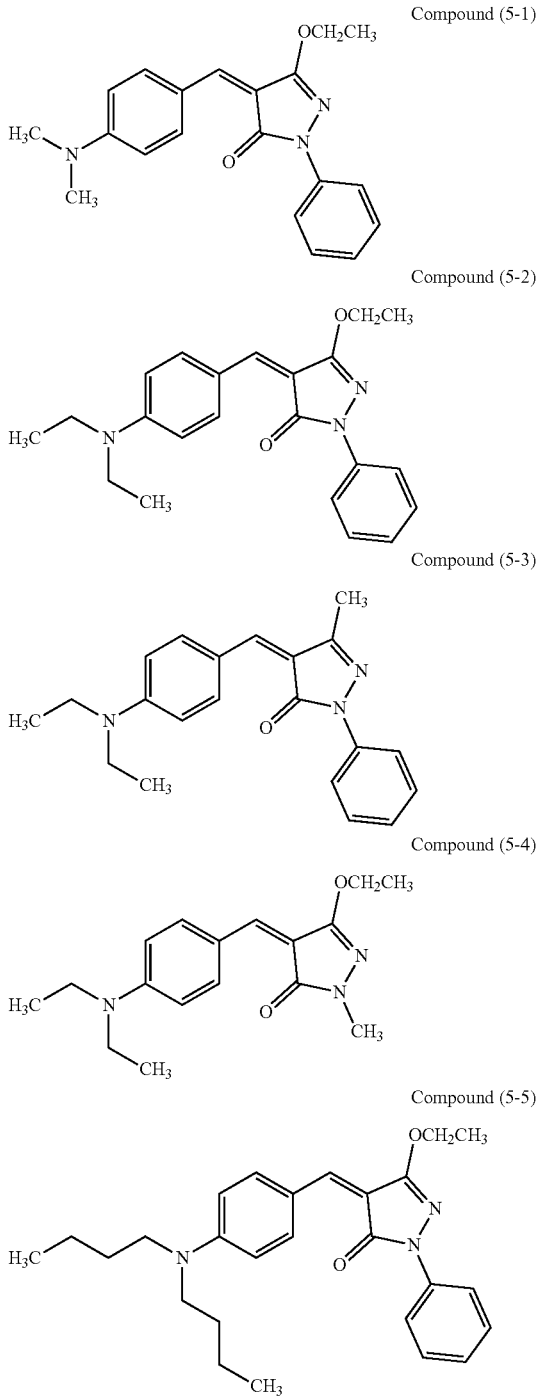

Compound (5-1)

Compound (5-2)

Compound (5-3)

Compound (5-4)

Compound (5-5)

As the yellow dye, among the compounds of Formula (5), at least one of the compounds (5-1), (5-2), and (5-5) is preferably used because images having excellent light resistance are easily obtained while maintaining high chroma.

Incidentally, as the yellow dye, a known yellow dye may be used in combination with these compounds of Formulae (3) to (5).

(iii) Magenta Dye (Compounds of Formulae (6) to (8))

The magenta layer of the thermal transfer recording sheet contains one or more compounds selected from the group of compounds represented by the following Formulae (6) to (8) as the magenta dye. That is, as the magenta dye, these compounds may be used alone or in combination of two or more thereof.

(iii-1) Compound of Formula (6)

Next, the compound (magenta dye) represented by Formula (6) will be described.

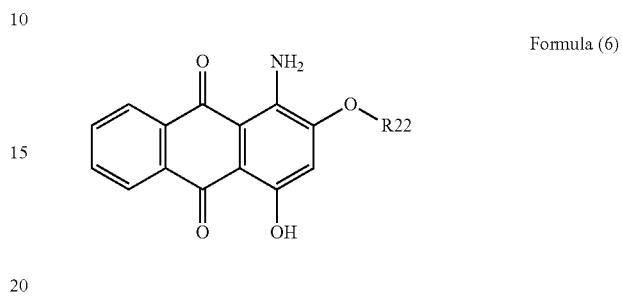

Formula (6)

[In Formula (6), R22 represents an alkyl group not having a substituent, an alkyl group substituted with an alkoxy group, or an aryl group optionally having a substituent.]

In Formula (6), the alkyl group represented by R22 is not particularly limited. Examples of the alkyl group include linear, branched, or cyclic primary to tertiary alkyl groups having 1 to 20 carbon atoms.

More specifically, examples of the alkyl group include a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, and a 2-ethylhexyl group. Among these alkyl groups, linear or branched alkyl groups having 1 to 8 carbon atoms are preferable because images having excellent light resistance are easily obtained while maintaining high chroma. For example, a methyl group and a 2-ethylhexyl group can be mentioned. In addition, alkyl groups having 2 to 8 carbon atoms and substituted with an alkoxy group are preferable. Specifically, for example, an ethoxyethoxyethyl group can be mentioned.

In Formula (6), the aryl group optionally having a substituent represented by R22 is not particularly limited as long as it is a substituted or unsubstituted aryl group. As the substituent, for example, an alkyl group and an alkoxy group can be mentioned. In addition, the total number of carbon atoms (including the number of carbon atoms of the substituent) of the aryl group can be, for example, 6 to 10.

Examples of the aryl group optionally having a substituent include a phenyl group, a tolyl group (2-methylphenyl group, 3-methylphenyl group, or 4-methylphenyl group), a naphthyl group, and a p-methoxyphenyl group. Among these aryl groups, a phenyl group, a tolyl group, a methoxyphenyl group, and a naphthyl group are preferable because images having excellent light resistance are easily obtained while maintaining high chroma. Furthermore, in particular, a phenyl group and a 3-methylphenyl group are more preferable.

As examples of the compound represented by Formula (6), compounds (6-1) to (6-9) are shown below, but the compound is not limited to the following compounds.

Compound (6-1)
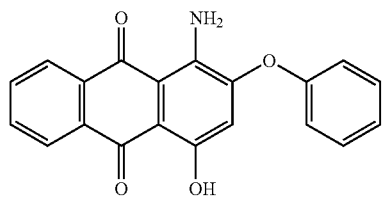

Compound (6-2)
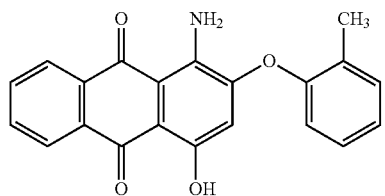

Compound (6-3)
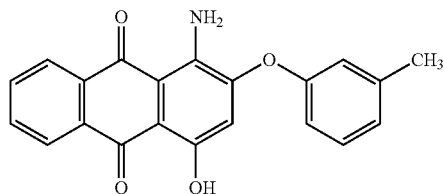

Compound (6-4)
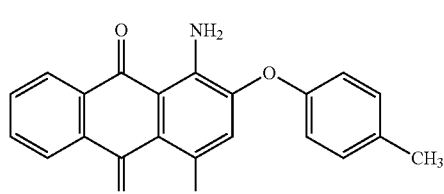

Compound (6-5)
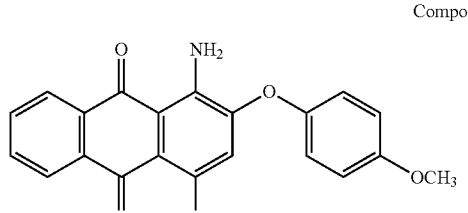

Compound (6-6)
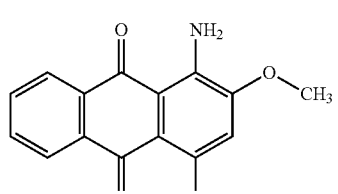

Compound (6-7)
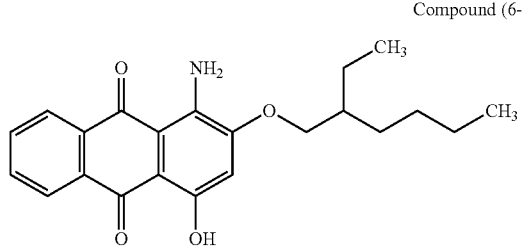

Compound (6-8)
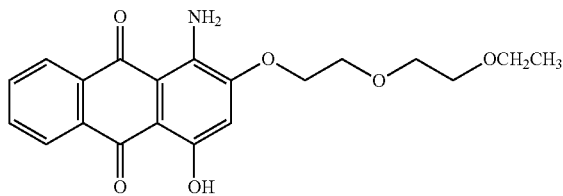

Compound (6-9)
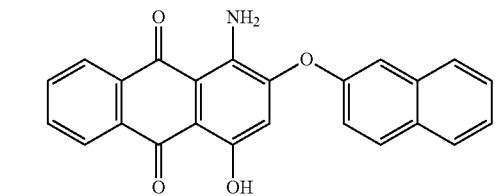

As the magenta dye, among the compounds of Formula (6), it is preferable to use at least one of compounds (6-1) to (6-5). In addition, it is more preferably to use one or both of compounds (6-1) and (6-3) as the compound of Formula (6) because images having excellent light resistance are easily obtained while maintaining high chroma.

(iii-2) Compound of Formula (7)

Then, the compound (magenta dye) represented by Formula (7) will be described.

Formula (7)
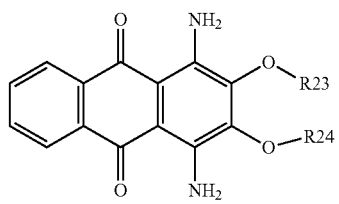

[In Formula (7), R23 and R24 each independently represent an alkyl group or an aryl group optionally having a substituent.]

In Formula (7), the alkyl group represented by R23 or R24 is not particularly limited. As the alkyl group, for example, those mentioned as R15 of Formula (4) can be similarly mentioned. In addition, among these alkyl groups, linear alkyl groups having 1 to 4 carbon atoms (e.g., a methyl group and a butyl group) are preferable because images having excellent light resistance are easily obtained while maintaining high chroma.

In Formula (7), the aryl group optionally having a substituent represented by R23 or R24 is not particularly limited as long as it is a substituted or unsubstituted aryl group. As the substituent, for example, an alkyl group can be mentioned. In addition, the total number of carbon atoms (including the number of carbon atoms of the substituent) of the aryl group can be, for example, 6 to 10. Examples of the aryl group optionally having a substituent include a phenyl group, a tolyl group (2-methylphenyl group, 3-methylphenyl group, or 4-methylphenyl group), a xylyl group (e.g., 3,5-dimethylphenyl group), a naphthyl group, and a p-(n-butyl) phenyl group. Among these aryl groups, a phenyl group, a tolyl group (e.g., 4-methylphenyl group), and a xylyl group (e.g., 3,5-dimethylphenyl group) are preferable because images having excellent light resistance are easily obtained while maintaining high chroma.

As examples of the compound represented by Formula (7), compounds (7-1) to (7-9) are shown below, but the compound is not limited to the following compounds.

Compound (7-1)

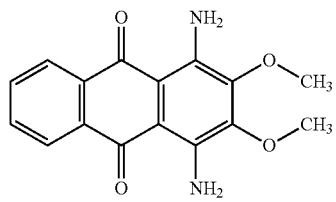

Compound (7-2)

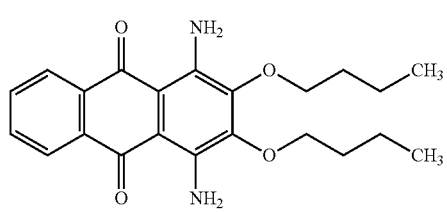

Compound (7-3)

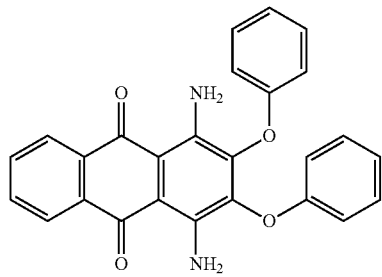

Compound (7-4)

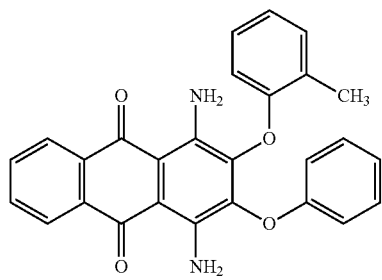

Compound (7-5)

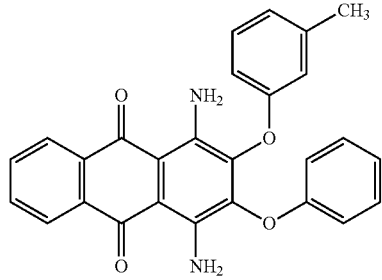

Compound (7-6)

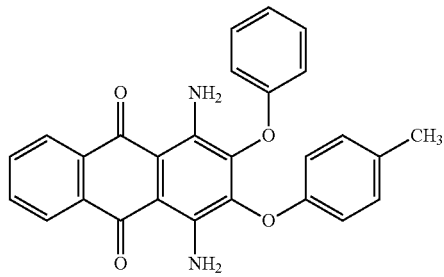

Compound (7-7)

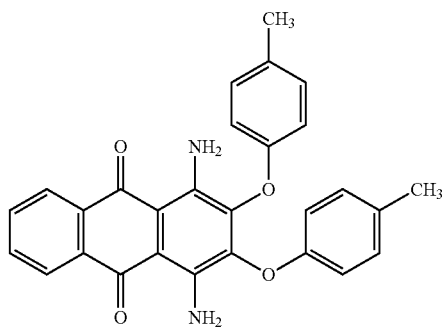

Compound (7-8)

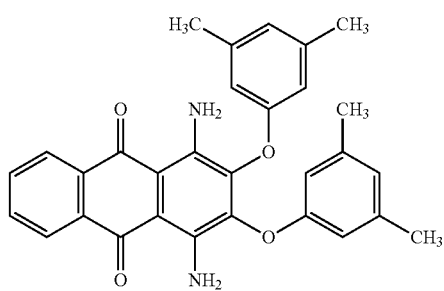

Compound (7-9)

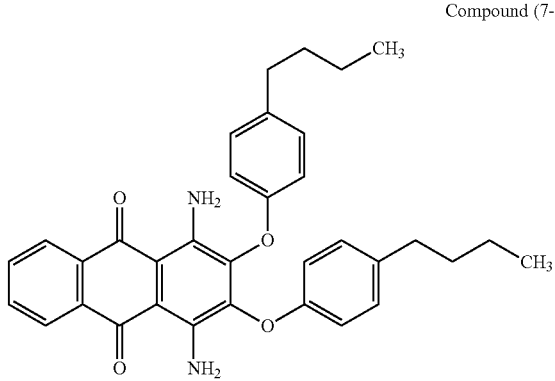

As the magenta dye, among the compounds of Formula (7), it is preferable to use at least one of the compounds (7-1) to (7-8). In addition, as the compounds of Formula (7), it is more preferable to use at least one of the compounds (7-3), (7-7), and (7-8) because images having excellent light resistance are easily obtained while maintaining high chroma.

(iii-3) Compound of Formula (8)

Then, the compound (magenta dye) represented by Formula (8) will be described.

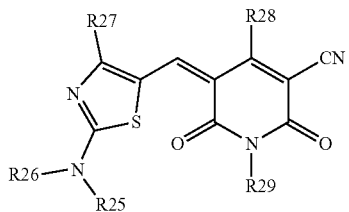

Formula (8)

[In Formula (8), R25 and R26 each independently represent an alkyl group; R27 represents a hydrogen atom, an alkyl group, or an aryl group optionally having a substituent; R28 represents an alkyl group or an aryl group optionally having a substituent; and R29 represents a hydrogen atom, an alkyl group, an aryl group optionally having a substituent, or —N(—R30)R31, where R30 and R31 each independently represent a hydrogen atom, an alkyl group, an aryl group, or an acyl group or represent a cyclic structure formed by binding of R30 and R31 to each other.]

In Formula (8), the alkyl group represented by R25 or R26 is not particularly limited as long as it is an alkyl group. As the alkyl group, for example, linear, branched, or cyclic primary to tertiary alkyl groups having 1 to 20 carbon atoms are mentioned. More specifically, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-butylbutyl group, a 2-ethylpropyl group, and a 2-ethylhexyl group are mentioned.

Incidentally, among these alkyl groups, branched alkyl groups, such as a 2-butylbutyl group and a 2-ethylhexyl group, are preferable because images having excellent light resistance are easily obtained while maintaining high chroma.

In Formula (8), the alkyl group represented by R27 is not particularly limited as long as it is an alkyl group. As the alkyl group, for example, those mentioned as R15 of Formula (4) can be similarly mentioned. In addition, among these alkyl groups, a tert-butyl group is preferable because images having excellent light resistance are easily obtained while maintaining high chroma.

In Formula (8), the aryl group optionally having a substituent represented by R27 is not particularly limited as long as it is a substituted or unsubstituted aryl group. As the substituent, for example, alkyl groups, such as a methyl group and an ethyl group; and alkoxy groups, such as a methoxy group, are mentioned. In addition, the total number of carbon atoms (including the number of carbon atoms of the substituent) of the aryl group can be, for example, 6 to 12. As the aryl group optionally having a substituent, for example, a phenyl group, a tolyl group (2-methylphenyl group, 3-methylphenyl group, or 4-methyl phenyl group), a xylyl group (e.g., 2,6-dimethylphenyl group), a 2,6-diethylphenyl group, a 3-methoxyphenyl group, a 2,6-dimethoxyphenyl group, a 2,4,6-trimethylphenyl group, and a 2,4,6-triethyl phenyl group are mentioned. In addition, among these aryl groups, a phenyl group is preferable because images having excellent light resistance and improved imbalance are easily obtained.

As described above, R27 is preferably a phenyl group or a tert-butyl group and is particularly preferably a tert-butyl group.

In Formula (8), the alkyl group represented by R28 is not particularly limited as long as it is an alkyl group. As the alkyl group, for example, linear or branched primary to tertiary alkyl groups having 1 to 8 carbon atoms (e.g., the number of carbon atoms of the main chain is 1 to 4) are mentioned. More preferably, for example, a methyl group, an ethyl group, an n-propyl group, an iso-propyl group, an n-butyl group, an iso-butyl group, a 2-methylbutyl group, and a 2,3,3-trimethylbutyl group are mentioned. Among these alkyl groups, a methyl group is preferable because images having excellent light resistance are easily obtained while maintaining high chroma.

In Formula (8), the aryl group optionally having a substituent represented by R28 is not particularly limited as long as it is a substituted or unsubstituted aryl group. As the substituent, for example, alkyl groups, such as a methyl group; and alkoxy groups, such as a methoxy group, are mentioned. In addition, the total number of carbon atoms (including the number of carbon atoms of the substituent) of the aryl group can be, for example, 6 to 8. Examples of the aryl group optionally having a substituent include a phenyl group, a tolyl group (2-methylphenyl group, 3-methylphenyl group, or 4-methylphenyl group), a 4-methoxyphenyl group, and a xylyl group (e.g., 3,5-dimethylphenyl group). In addition, among these aryl groups, a phenyl group is preferably because images having excellent light resistance are easily obtained while maintaining high chroma.

In Formula (8), the alkyl group represented by R29 is not particularly limited as long as it is an alkyl group. As the alkyl group, for example, linear or branched primary to tertiary alkyl groups having 1 to 8 carbon atoms are mentioned. More specifically, for example, a methyl group, an ethyl group, an n-propyl group, an iso-propyl group, an n-butyl group, and an iso-butyl group are mentioned. Among these alkyl groups, a methyl group is preferable because images having excellent light resistance are easily obtained while maintaining high chroma.

In Formula (8), the aryl group optionally having a substituent represented by R29 is not particularly limited as long as it is a substituted or unsubstituted aryl group. As the substituent, for example, alkyl groups, such as a methyl group, and alkoxy groups, such as a methoxy group, can be mentioned. In addition, the total number of carbon atoms (including the number of carbon atoms of the substituent) of the aryl group can be, for example, 6 to 12. As the aryl group optionally having a substituent, for example, a phenyl group and a naphthyl group are mentioned. In addition, among these aryl groups, a phenyl group is preferable because images having excellent light resistance are easily obtained while maintaining high chroma.

In Formula (8), when R29 is —N(—R30)R31, the alkyl group represented by R30 or R31 is not particularly limited as long as it is an alkyl group. As the alkyl group, for example, those mentioned as R15 of Formula (4) can be similarly mentioned. In addition, among these alkyl groups, a methyl group is preferable because images having excellent light resistance and improved imbalance are easily obtained.

In Formula (8), when R29 is —N(—R30)R31, the aryl group represented by R30 or R31 is not particularly limited as long as it is an aryl group. As the aryl group, for example, a phenyl group and a naphthyl group can be mentioned. In addition, among these aryl groups, a phenyl group is preferable because images having excellent light resistance and improved imbalance are easily obtained.

In Formula (8), when R28 is —N(—R30)R31, the acyl group represented by R30 or R31 is not particularly limited as long as it is an acyl group. As the acyl group, for example, an unsubstituted alkylcarbonyl group having 2 to 30 carbon atoms, a substituted or unsubstituted arylcarbonyl group having 7 to 30 carbon atoms, and —C(=O)-A (A represents a hetero ring) are mentioned. More specifically, for example, an acetyl group, a propionyl group, a pivaloyl group, a benzoyl group, and a naphthoyl group are mentioned. In addition, as —C(=O)-A, for example, a 2-pyridylcarbonyl group and a 2-furylcarbonyl group are mentioned. Incidentally, examples of the substituent of the arylcarbonyl group include alkyl groups having 1 to 4 carbon atoms and alkoxy groups having 1 to 4 carbon atoms.

In Formula (8), when R29 is —N(—R30)R31, the cyclic structure formed by binding of R30 and R31 to each other is not particularly limited as long as it is a cyclic structure. As the cyclic structure, for example, a piperidine ring, a piperazine ring, and a morpholine ring are mentioned.

Incidentally, among these compounds, at least one of R30 and R31 is preferably an alkyl group because the light resistance is excellent. Furthermore, at least one of R30 and R31 is preferably a methyl group because images having excellent light resistance are easily obtained while maintaining high chroma.

As examples of the compound represented by Formula (8), compounds (8-1) to (8-11) are shown below, but the compound is not limited to the following compounds.

Compound (8-1)

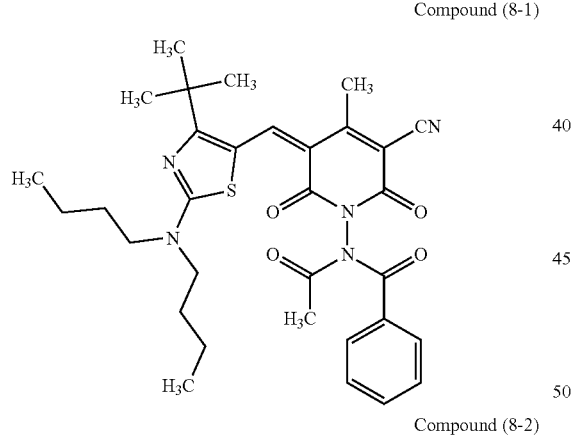

Compound (8-2)

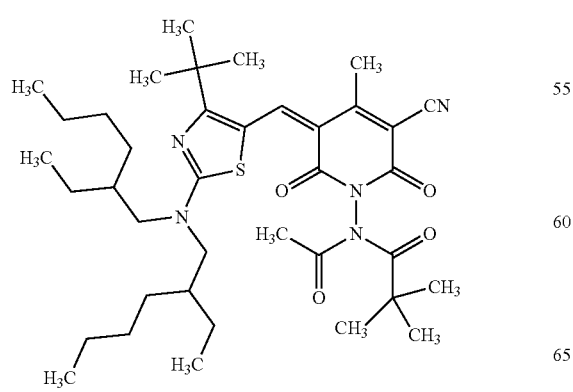

Compound (8-3)

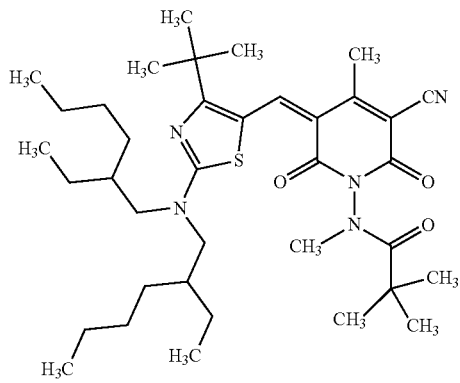

Compound (8-4)

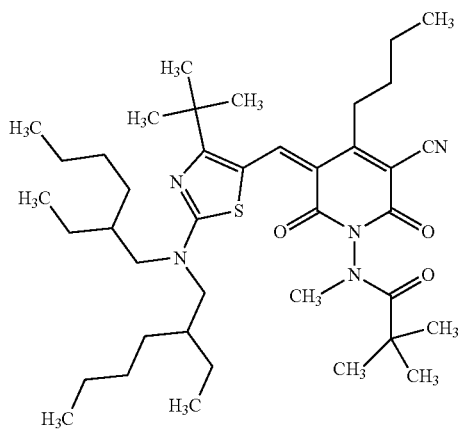

Compound (8-5)

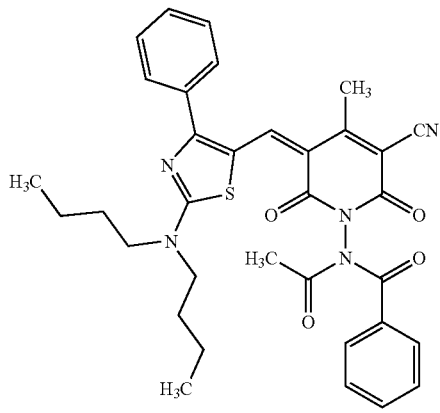

Compound (8-6)
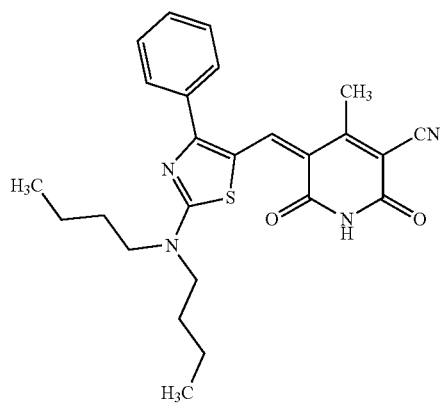
Compound (8-7)
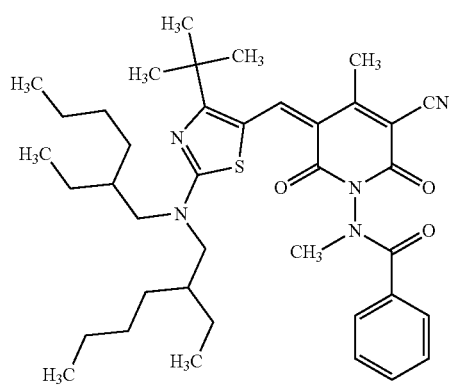
Compound (8-8)
Compound (8-9)
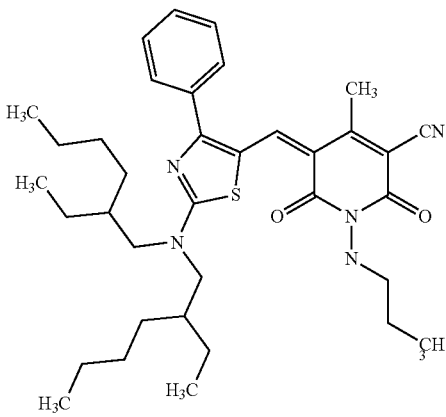
Compound (8-10)
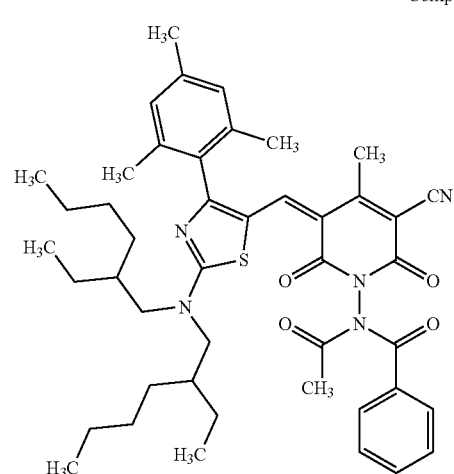
Compound (8-11)
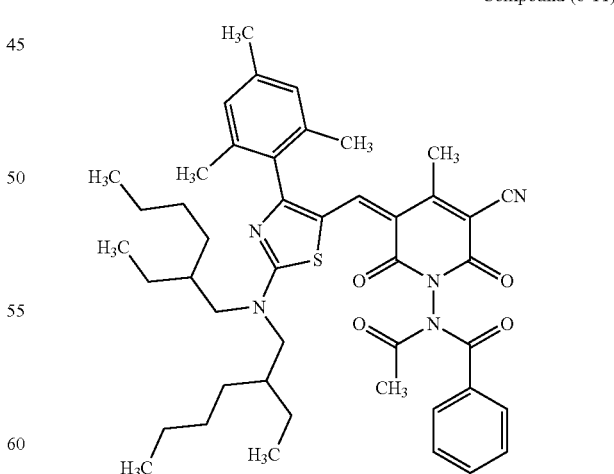
As the compound of Formula (8), it is preferable to use at least one of compounds (8-1) to (8-3) and (8-7) because images having excellent light resistance are easily obtained while maintaining high chroma.

Incidentally, as the magenta dye, a known magenta dye may be used in combination with these compounds of Formulae (6) to (8).

The amount of the color material to be used is 1 to 150 parts by mass based on 100 parts by mass of the binder resin contained in the color material layer and is preferably 50 to 120 parts by mass from the viewpoint of dispersibility of the color material in a dispersion. Incidentally, when a mixture of two or more color materials is used, the total amount is preferably within the above-mentioned range.

Binder Resin

The binder resin is not particularly limited, and preferable examples thereof include water-soluble resins, such as a cellulose resin, a polyacrylic acid resin, a starch resin, and an epoxy resin; and organic solvent-soluble resins, such as a polyacrylic resin, a polymethacrylic resin, a polystyrene resin, a polycarbonate resin, a polyether sulfone resin, a polyvinyl butyral resin, an ethyl cellulose resin, an acetyl cellulose resin, a polyester resin, an AS resin, and a phenoxy resin. These resins may be used alone or in combination of two or more thereof as needed.

Surfactant

The color material layer may contain a surfactant for providing sufficient lubrication when a thermal head is heated (during printing).

Wax

The color material layer may contain wax for providing sufficient lubrication when a thermal head is not heated. Examples of the wax to be added include, but not limited to, polyethylene wax, paraffin wax, and fatty acid ester wax.

Other Component

The color material layer may contain, in addition to the above additives, for example, an ultraviolet absorber, a preservative, an antioxidant, an antistatic agent, and a viscosity modifier as needed.

Medium

When the color material layer is formed, the medium that is used for preparing a dispersion is not particularly limited, and examples thereof include water and an organic solvent. Preferred examples of the organic solvent include alcohols, such as methanol, ethanol, isopropanol, and isobutanol; cellosolves, such as methyl cellosolve and ethyl cellosolve; aromatic hydrocarbons, such as toluene, xylene, and chlorobenzene; esters, such as ethyl acetate and butyl acetate; ketones, such as acetone, methyl ethyl ketone, methyl isobutyl ketone, and cyclohexanone; halogenated hydrocarbons, such as methylene chloride, chloroform, and trichloroethylene; ethers, such as tetrahydrofuran and dioxane; N,N-dimethylformamide; and N-methylpyrrolidone. These organic solvents may be used alone or in combination of two or more thereof as needed.

Substrate

Subsequently, the substrate constituting a thermal transfer recording sheet will be described. The substrate supports the color material layer and is not particularly limited as long as it is a film having certain heat resistance and strength, and a known substrate can be used. Examples thereof include a polyethylene terephthalate film, a polyethylene naphthalate film, a polycarbonate film, a polyimide film, a polyamide film, an aramide film, a polystyrene film, a poly(1,4-cyclohexylene dimethylene terephthalate) film, a polysulfone film, a polypropylene film, a polyphenylene sulfide film, a polyvinyl alcohol film, cellophane, a cellulose derivative, a polyethylene film, a polyvinyl chloride film, a nylon film, condenser paper, and paraffin paper. Among these substrates, a polyethylene terephthalate film is preferable from the viewpoint of mechanical strength, solvent resistance, and economical efficiency.

The thickness of the substrate is 0.5 to 50 µm and is preferably 3 to 10 µm from the viewpoint of transferability.

When a coating solution containing a dye is applied on the substrate for forming a color material layer, for example, the wettability and adhesiveness of the coating solution tend to be insufficient. Accordingly, the surface of the substrate on which the color material layer is formed (formation surface) is preferably subjected to adhesive treatment, as needed. The formation surface of the color material layer may be one surface or both surfaces of the substrate. Although the adhesive treatment is not particularly limited, examples thereof include ozone treatment, corona discharge treatment, UV light treatment, plasma treatment, low-temperature plasma treatment, primer treatment, and chemical agent treatment. In addition, these treatments may be performed in combination.

As the adhesive treatment of the substrate, an adhesive layer may be coated on the substrate. Although the adhesive layer is not particularly limited, for example, fine particles of an organic material such as a polyester resin, a polystyrene resin, a polyacrylic ester resin, a polyamide resin, a polyether resin, a polyvinyl acetate resin, a polyethylene resin, a polypropylene resin, a polyvinyl chloride resin, a polyvinyl alcohol resin, or a polyvinyl butyral resin or fine particles of an inorganic material such as silica, alumina, magnesium carbonate, magnesium oxide, or titanium oxide can be used.

Since the thermal transfer recording sheet of the present invention contains a compound represented by Formula (1), it is possible to provide a thermal transfer recording sheet showing cyan color having high chroma, high light resistance, and excellent storage stability.

Resist Composition for Color Filter, and Color Filter

Subsequently, a resist composition for a color filter according to the present invention (hereinafter, also referred to as "resist composition of the present invention") will be described. The compound represented by Formula (1) having excellent light resistance while maintaining high chroma is suitable for toning the resist composition for a color filter. In addition, a color filter having excellent light resistance can be obtained while maintaining high chroma by using the resist composition of the present invention.

The resist composition for a color filter of the present invention contains a binder resin, a medium, and the compound of the present invention as a colorant. The resist composition for a color filter of the present invention is obtained as follows. The compound of the present invention and the binder resin are added to the medium while stirring. At this time, a polymerizable monomer, a polymerization initiator, a photoacid generator, etc. may be added as needed. Subsequently, a mechanical shear force is applied to the mixture using a disperser for stably dissolving or finely dispersing the above-mentioned materials in the medium. The resist composition for a color filter of the present invention can thereby be obtained.

Binder Resin

The binder resin that can be used in the resist composition of the present invention may be any one as long as either one of the light irradiation part and the light shielding part in the light exposure process at the time of pixel formation is soluble in an organic solvent, an alkali aqueous solution, water, or a commercially available developing solution. In particular, a binder resin having a composition that allows development in water or an alkali aqueous solution is preferable from the viewpoint of workability and in ease of treatment after resist production.

As the binder resin, a binder resin prepared by copolymerizing a hydrophilic polymerizable monomer, such as acrylic acid, methacrylic acid, N-(2-hydroxyethyl)acrylamide, N-vinylpyrrolidone, or a polymerizable monomer including an ammonium salt, and a lipophilic polymerizable monomer, such as acrylic acid ester, methacrylic acid ester, vinyl acetate, styrene, or N-vinylcarbazole, at an appropriate mixing ratio by a known method can be used. These binder resins are used in combination with a radical polymerizable monomer having an ethyleny unsaturated group, a cationic polymerizable monomer having an oxirane ring or an oxetane ring, a radical-generating agent, an acid-generating agent, and a base-generating agent. Such a binder resin can be used as a negative-type resist composition for removing only the light-shielded portion by developing, because this binder resin decreases the solubility of the material of the exposure portion in a developing solution by exposure to light.

In addition, a combination of a resin having a quinone diazide group being cleaved by light and generating carboxylic acid or a resin having a group that is cleaved by an acid, such as tert-butylcarbonate of polyhydroxystyrene or tetrahydropyranyl ether, and an acid-generating agent that generates an acid by exposure to light can be used. Such a resin can be used as a positive-type resist composition for removing only the exposure portion by developing, because, in the exposure portion, the solubility of the material to the developing solution improves by exposure to light.

When the resist composition of the present invention is the negative-type resist composition, it is preferable to use a polymerizable monomer that is addition-polymerized by exposure to light (hereinafter, also referred to as a "photopolymerizable monomer") as the binder resin. The photopolymerizable monomer is preferably a compound having at least one addition polymerizable ethyleny unsaturated double bond in the molecule and having a boiling point of 100° C. or more at ordinary pressure. Specifically, examples thereof include monofunctional acrylates and methacrylates, such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; multifunctional acrylates and methacrylates, such as polyethylene glycol diacrylate, polyethylene glycol dimethacrylate, polypropylene glycol diacrylate, polypropylene glycol dimethacrylate, trimethylol ethane triacrylate, trimethylol ethane trimethacrylate, trimethylol propane triacrylate, trimethylol propane trimethacrylate, trimethylol propane diacrylate, trimethylol propane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylol propane tri(acryloyloxypropyl)ether, tri(acryloyloxyethyl)isocyanurate, tri(acryloyloxyethyl) cyanurate, glycerol triacrylate, and glycerol trimethacrylate; and multifunctional acrylates and multifunctional methacrylates obtained by adding ethylene oxide or propylene oxide to a multifunctional alcohol such as trimethylol propane or glycerol and then performing acrylation or methacrylation. Furthermore, multifunctional epoxy acrylates and epoxy methacrylates, which are reaction products of urethane acrylates, polyester acrylates, and an epoxy resin with acrylic acid or methacrylic acid, can also be used.

Among the above-mentioned photopolymerizable monomers, it is preferable to use trimethylol propane triacrylate, trimethylol propane trimethacrylate, pentaerythritol tetraacrylate, pentaerythritol tetramethacrylate, dipentaerythritol hexaacrylate, dipentaerythritol hexamethacrylate, dipentaerythritol pentaacrylate, or dipentaerythritol pentamethacrylate. The above-mentioned photopolymerizable monomers may be used alone or in combination of two or more thereof as needed.

The content of the photopolymerizable monomer is preferably 5 to 50 mass %, more preferably 10 to 40 mass %, based on the mass (the total solid content) of the resist composition according to the present invention. When the content is within the above-mentioned range, the sensitivity to exposure light can be further improved, and also the resist composition has good adhesiveness.

When the resist composition of the present invention is the negative-type resist composition, the composition may contain a photopolymerization initiator. Examples of the photopolymerization initiator include a vicinal polyketoaldol compound, an α-carbonyl compound, an acyloin ether, a diverse quinone compound, a combination of a triallylimidazole dimer and p-aminophenylketone, and a trioxadiazole compound. Among these initiators, 2-benzyl-2-dimethylamino-1-(4-morpholinophenyl)butanone (trade name: Irgacure 369, manufactured by BASF AG) is preferable. Incidentally, when electron rays are used in formation of pixels by the resist composition of the present invention, the photopolymerization initiator is not essential.

In addition, when the resist composition of the present invention is the positive-type resist composition, the composition may contain a photoacid generator as needed. As the photoacid generator, a known photoacid generator, for example, a salt of an anion and an onium ion, such as a sulfonium, iodonium, selenium, ammonium, or phosphonium ion, can be used.

Examples of the sulfonium ion include triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Examples of the iodonium ion include diphenyliodonium, di-p-tolyliodonium, bis(4-dodecylphenyl)iodonium, bis(4-methoxyphenyl)iodonium, and (4-octyloxyphenyl)phenyliodonium.

Examples of the selenium ion include triarylseleniums, such as triphenylselenium, tri-p-tolylselenium, tri-o-tolylselenium, tris(4-methoxyphenyl)selenium, 1-naphtyldiphenylselenium, tris(4-fluorophenyl)selenium, tri-1-naphthylselenium, and tri-2-naphthylselenium.

Examples of the ammonium ion include tetraalkylammoniums, such as tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, and trimethylisobutylammonium.

Examples of the phosphonium ion include tetraphenylphosphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

Examples of the anion include, but not limited to, perhalogenic acid ions, such as $ClO_4^-$ and $BrO_4^-$; halogenated sulfonate ions, such as $FSO_3^-$ and $ClSO_3^-$; sulfate ions, such as $CH_3SO_4^-$, $CF_3SO_4^-$, and $HSO_4^-$; carbonate ions, such as $HCO_3^-$ and $CH_3CO_3^-$; aluminate ions, such as $AlCl_4^-$ and $AlF_4^-$; a hexafluorobismuthate ion; carboxylate ions, such as $CH_3COO^-$, $CF_3COO—$, $C_6H_5COO^-$, $CH_3C_6H_4COO^-$, $C_6F_5COO^-$, and $CF_3C_6H_4COO^-$; arylborate ions, such as $B(C_6H_5)_4^-$ and $CH_3CH_2CH_2CH_2B(C_6H_5)_3^-$; a thiocyanate ion; and a nitrate ion.

Medium

In the resist composition of the present invention, water or an organic solvent can be used as the medium for dissolving or dispersing the compound of the present invention, the binder resin, and a photopolymerizable monomer, a photopolymerization initiator, and a photoacid generator that are added as needed. Examples of the organic solvent include cyclohexanone, ethyl cellosolve acetate, butyl cellosolve acetate, 1-methoxy-2-propyl acetate, diethylene glycol dimethyl ether, ethyl benzene, 1,2,4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropanol, butanol, methyl isobutyl ketone, and a petroleum solvent. These solvents may be used alone or in combination of two or more thereof.

Colorant

As the colorant constituting the resist composition of the present invention, a compound represented by Formula (1) is used, and compounds represented by Formula (1) may be used alone or in combination of two or more thereof. In addition, in order to obtain desired spectral characteristics, another dye may be used in combination for toning. Although the dye that can be used in combination is not particularly limited, examples thereof include a condensed azo compound, an azo metal complex, a diketopyrrolopyrrole compound, an anthraquinone compound, a quinacridone compound, a naphthol compound, a benzimidazolone compound, a thioindigo compound, a perylene compound, a methine compound, an allylamide compound, and a basic dye lake compound.

The resist composition for a color filter of the present invention may contain, in addition to the above-mentioned additives, an ultraviolet absorber and a silane coupling agent for improving adhesiveness with a glass substrate when the filter is produced, as needed.

Although the disperser is not particularly limited, a rotation shearing-type homogenizer, a media type disperser such as a ball mill, a sand mill, or an attritor, or a high-pressure counter-collision type disperser can be used.

As described above, the resist composition for a color filter of the present invention includes the compound represented by Formula (1) having excellent light resistance while maintaining high chroma and is therefore a resist composition for a color filter having excellent light resistance while maintaining high chroma. Incidentally, in a color filter where two or more types of pixels having different spectral characteristics are arranged so as to be adjacent to each other, a color filter having excellent light resistance can be obtained while maintaining high chroma by using the resist composition of the present invention in pixels constituting at least one color among a plurality of colors (e.g., red, green, and blue) of the pixels.

Toner

Subsequently, a toner according to the present invention will be described. The compound of the present invention having excellent light resistance while maintaining high chroma can be suitably used in a toner.

The toner of the present invention contains a binder resin and the compound represented by Formula (1). In addition, the toner contains, for example, another colorant, magnetic substance, wax, a charge control agent, and other additives, as needed. Examples of the method for manufacturing toner particles constituting the toner of the present invention include a grinding method, a suspension polymerization method, a suspension granulation method, an emulsion polymerization method, and an emulsion aggregation method. In addition, the toner of the present invention can also be used by adding to a developer to be used in a liquid development. Among these methods, the toner of the present invention using the compound represented by Formula (1) as the colorant is preferably a ground toner manufactured by a grinding method.

Incidentally, as the colorant, a compound represented by Formula (1) is used, and compounds represented by Formula (1) may be used alone or in combination of two or more thereof. In addition, a known pigment or dye may be used in combination for adjusting, for example, the color tone, according to the method for manufacturing a toner.

Each component constituting a toner will now be described.

Colorant

As a colorant, it is preferable to use a combination of a compound represented by Formula (1) and a known pigment for a toner (e.g., C.I. Pigment Blue 15:3).

The compound represented by Formula (1) is preferably used within a range of 0.01 to 1.0 parts by mass, preferably 0.03 to 0.5 parts by mass, and particularly preferably 0.05 to 0.2 parts by mass based on 100 parts by mass of the binder resin.

Although the colorant that can be further used in combination is not particularly limited, examples thereof include a condensed azo compound, an azo metal complex, a diketopyrrolopyrrole compound, an anthraquinone compound, a quinacridone compound, a naphthol compound, a benzimidazolone compound, a thioindigo compound, a perylene compound, a methine compound, an allylamide compound, and a basic dye lake compound.

Binder Resin

Examples of the binder resin used in the toner of the present invention include a vinyl resin, a polyester resin, an epoxy resin, a polyurethane resin, a polyvinyl butyral resin, a terpene resin, a phenolic resin, an aliphatic or alicyclic hydrocarbon resin, an aromatic petroleum resin, rosin, and modified rosin. Among these binder resins, from the viewpoint of electrostatic property and fixability, a vinyl resin and a polyester resin are preferable, and use of a polyester resin is more preferable because the effects of electrostatic property and fixability are further increased. These resins may be used alone or in combination of two or more thereof. When a mixture of two or more resins is used, it is preferable to mix resins having different molecular weights for controlling the viscoelastic property of the toner.

The binder resin preferably has a glass transition temperature (Tg) of 45° C. to 80° C., more preferably 55° C. to 70° C., and a number average molecular weight (Mn) of 1,500 to 50,000 and weight average molecular weight (Mw) of 6,000 to 1,000,000.

When a polyester resin is used as the binder resin, although not particularly limited to, the molar ratio of the alcohol component to the acid component in the entire components is preferably 45/55 to 55/45. The environmental dependence of the charging characteristics of a toner is increased with an increase in the number of terminal groups of the molecular chains of the polyester resin.

Accordingly, the acid value is preferably 90 mg KOH/g or less and more preferably 50 mg KOH/g or less. In addition, the hydroxyl value is preferably 50 mg KOH/g or less and more preferably 30 mg KOH/g or less.

Wax

The toner of the present invention may contain wax as needed. Examples of the wax include, but not limited to, polyethylene wax, paraffin wax, and fatty acid ester wax.

Charge Control Agent

The toner of the present invention may be mixed with a charge control agent as needed. Although the charge control agent is not particularly limited, examples of the agent of controlling the toner to negative charge include polymers or copolymers having sulfonic acid groups, sulfonate groups, or sulfonic acid ester groups, salicylic acid derivatives and metal complexes thereof, monoazo metal compounds, acetylacetone metal compounds, aromatic oxycarboxylic acids, aromatic mono- or poly-carboxylic acids and metal salts, anhydrides, and esters thereof, phenol derivatives such as bisphenol, urea derivatives, metal-containing naphthoic acid compounds, boron compounds, quaternary ammonium salts, calixarene, and resin charge control agents.

In addition, examples of the agent of controlling the toner to positive charge include nigrosine and fatty acid metal salt-modified nigrosine, guanidine compounds, imidazole compounds, quaternary ammonium salts such as tributylbenzylammonium-1-hydroxy-4-naphthosulfonate and tetrabutylammonium tetrafluoroborate, analogs thereof, i.e., an onium salt such as a phosphonium salt, and lake pigments thereof, a triphenylmethane dye and lake pigments thereof (laking agent is, for example, phosphotungstic acid, phosphomolybdenic acid, phosphotungstomolybdenic acid, tannic acid, lauric acid, gallic acid, a ferricyanide, or a ferrocyanide), metal salts of higher fatty acids, diorganotin oxides such as dibutyltin oxide, dioctyltin oxide, and dicyclohexyltin oxide, diorganotin borates such as dibutyltin borate, dioctyltin borate, and dicyclohexyltin borate, and resin charge control agents. These charge control agents may be used alone or in combination of two or more thereof.

EXAMPLES

The present invention will now be described in further detail with reference to examples and comparative examples but is not limited to these examples. Incidentally, in the text, the term "part(s)" means "part(s) by mass" unless otherwise specified. In addition, the resulting compound was identified with a $^1$H nuclear magnetic resonance spectrometric analysis ($^1$H-NMR) apparatus (AVANCE-600 NMR spectrometer, manufactured by BRUKER GmbH or AVANCE-500 NMR spectrometer, manufactured by BRUKER GmbH) and a high performance liquid chromatograph-mass spectrometer (LCMS-2010, manufactured by Shimadzu Corporation).

Manufacturing Example 1: Manufacturing of Compound (1-1)

A mixture solution of 48 mL of acetic acid of triazole compound (A-1) (5.00 g, 20.5 mmol), 12 mL of water, and 12 mL of concentrated hydrochloric acid was cooled to 0° C., and 2 mL of water of sodium nitrite (1.27 g, 18.4 mmol) was slowly dropwise added to the mixture so as to keep it at 5° C. or less, followed by stirring at 0° C. to 5° C. for 1 hour. Furthermore, the mixture was warmed to room temperature and was stirred for 1 hour. The precipitated solid was filtered and washed with 200 mL of water to obtain a nitroso compound (3.9 g, yield: 70.0%).

Thiazole compound (C-3) (3.17 g, 11.0 mmol) was added to a solution of 100 mL of chloroform of the resulting nitroso compound (3.00 g, 11.0 mmol), followed by stirring at room temperature for 24 hours. After completion of the reaction, the solvent was concentrated under reduced pressure, followed by purification by silica gel chromatography (eluent: ethyl acetate/heptane) to obtain a compound (1-1) (3.57 g, 59.8%). Compound (1-1) was identified by $^1$H-NMR analysis and mass spectrometry. FIGURE shows a $^1$H-NMR spectrum of compound (1-1) in $CDCl_3$ at room temperature at 600 MHz.

Result of Analysis of Compound (1-1)

[1] $^1$H-NMR (600 MHz, $CDCl_3$, room temperature): δ (ppm)=1.00-1.06 (6H, m), 1.09 (9H, s), 1.43-1.50 (4H, m), 1.79-1.84 (4H, m), 2.44 (3H, s), 2.80 (2H, s), 3.61-3.99 (2H, m), 4.00-4.01 (2H, m), 7.52 (2H, dd, J=6.6, 1.2 Hz), 7.59 (1H, d, J=7.8 Hz), 8.04 (2H, dd, J=7.2, 1.2 Hz).

[2] mass spectrometry (LCMS-2010): m/z=543.50 $(M+H)^+$.

Manufacturing Example 2: Manufacturing of Compound (1-2)

Compound (1-2) was manufactured as in Manufacturing Example 1 except that triazole compound (A-1) and thiazole compound (C-1) were used and was identified.

Result of Analysis of Compound (1-2)

[1] $^1$H-NMR (600 MHz, $CDCl_3$, room temperature): δ (ppm)=0.88-0.98 (12H, m), 1.09 (9H, s), 1.31-1.43 (6H, m), 1.54 (10H, s), 1.90-1.99 (1H, br), 2.0-2.08 (1H, br), 2.49 (3H, d, J=2.4 Hz), 3.80-3.90 (1H, br), 3.91-3.99 (1H, br), 7.52 (2H, d, J=8.4 Hz), 7.51-7.60 (1H, m), 8.20 (2H, d, J=9.0 Hz).

[2] mass spectrometry (LCMS-2010): m/z=655.55 $(M+H)^+$.

Manufacturing Example 3: Manufacturing of Compound (1-4)

Compound (1-4) was manufactured as in Manufacturing Example 1 except that triazole compound (A-3) and thiazole compound (C-1) were used and was identified.

Result of Analysis of Compound (1-4)

[1] $^1$H-NMR (600 MHz, $CDCl_3$, room temperature): δ (ppm)=0.89-1.98 (18H, m), 1.31-1.65 (14H, m), 1.90-2.08 (5H, m), 2.50 (3H, s), 2.89-2.92 (2H, m), 3.54 (2H, t, J=5.4 Hz), 3.87 (1H, br), 4.00 (1H, br), 7.53 (2H, d, J=7.2 Hz), 7.51-7.60 (1H, m), 8.04 (2H, d, J=7.8 Hz).

[2] mass spectrometry (LCMS-2010): m/z=641.50 $(M+H)^+$.

Manufacturing Example 4: Manufacturing of Compound (1-5)

Compound (1-5) was manufactured as in Manufacturing Example 1 except that triazole compound (A-2) and thiazole compound (C-1) were used and was identified.

Result of Analysis of Compound (1-5)

[1] $^1$H-NMR (600 MHz, $CDCl_3$, room temperature): δ (ppm)=0.95-1.02 (12H, m), 1.37-1.45 (11H, m), 1.62 (5H, s), 1.95-2.08 (2H, br), 2.55 (3H, s), 3.50 (2H, s), 3.88-3.97 (1H, br), 4.0-4.08 (1H, br), 4.31 (2H, d, J=3.6 Hz), 7.27-7.36 (3H, m), 7.46-7.47 (2H, m), 7.56-7.56 (2H, m), 7.61-7.67 (1H, m), 8.01 (2H, s).

[2] mass spectrometry (LCMS-2010): m/z=675.55 $(M+H)^+$.

Manufacturing Example 5: Manufacturing of Compound (1-6)

Compound (1-6) was manufactured as in Manufacturing Example 1 except that triazole compound (A-7) and thiazole compound (C-1) were used and was identified.
Result of Analysis of Compound (1-6)
[1] $^1$H-NMR (600 MHz, CDCl$_3$, room temperature): δ (ppm)=0.85-0.97 (12H, m), 1.25-1.41 (16H, m), 1.95 (2H, br), 2.05 (2H, br), 2.50 (3H, s), 3.24 (2H, br), 3.53 (2H, br), 3.82-3.91 (1H, br), 3.98-4.01 (1H, br), 7.25-7.30 (5H, m), 7.53-7.61 (3H, m), 8.06 (2H, d, J=7.2 Hz).
[2] mass spectrometry (LCMS-2010): m/z=689.55 (M+H)$^+$.

Manufacturing Example 6: Manufacturing of Compound (1-8)

Compound (1-8) was manufactured as in Manufacturing Example 1 except that triazole compound (A-4) and thiazole compound (C-1) were used and was identified.
Result of Analysis of Compound (1-8)
[1] $^1$H-NMR (500 MHz, CDCl$_3$, room temperature): δ (ppm)=0.88-0.99 (13H, m), 1.11 (12H, s), 1.31-1.49 (12H, m), 1.78 (3H, br), 1.95 (1H, br), 2.05 (1H, br), 2.82 (2H, s), 2.94-2.95 (2H, m), 3.53-3.54 (2H, br), 3.86-3.91 (1H, br), 3.95-4.00 (1H, br), 7.53 (2H, t, J=7.8 Hz), 7.61 (1H, s), 8.03 (2H, dd, J=7.2 Hz, 1.2 Hz).
[2] mass spectrometry (LCMS-2010): m/z=669.65 (M+H)$^+$.

Manufacturing Example 7: Manufacturing of Compound (1-10)

Compound (1-10) was manufactured as in Manufacturing Example 1 except that triazole compound (A-6) and thiazole compound (C-1) were used and was identified.
Result of Analysis of Compound (1-10)
[1] $^1$H-NMR (600 MHz, CDCl$_3$, room temperature): δ (ppm)=0.60-0.70 (3H, m), 0.81-1.00 (13H, m), 1.04-1.13 (12H, m), 1.22-1.49 (17H, m), 2.05 (2H, br), 2.71-2.81 (2H, br), 2.82-2.95 (2H, br), 3.42-3.57 (2H, br), 3.82-3.92 (1H, br), 3.93-4.01 (1H, br), 7.41-7.56 (2H, m), 7.57-7.61 (1H, m), 7.88-8.00 (2H, m).
[2] mass spectrometry (LCMS-2010): m/z=697.65 (M+H)$^+$.

Manufacturing Example 8: Manufacturing of Compound (1-12)

Compound (1-12) was manufactured as in Manufacturing Example 1 except that triazole compound (A-8) and thiazole compound (C-1) were used and was identified.
Result of Analysis of Compound (1-12)
[1] $^1$H-NMR (500 MHz, CDCl$_3$, room temperature): δ (ppm)=0.94-1.09 (12H, m), 1.12-1.15 (3H, m), 1.38-1.45 (16H, m), 1.90-2.10 (2H, br), 2.96-2.99 (2H, m), 3.42-3.60 (2H, br), 3.83-3.98 (1H, br), 3.99-4.09 (1H, br), 4.22-4.31 (2H, m), 7.25-7.35 (3H, m), 7.32-7.36 (2H, m), 7.43-7.47 (2H, m), 7.55-7.58 (1H, m), 8.04 (2H, t, J=7.0 Hz).
[2] mass spectrometry (LCMS-2010): m/z=689.50 (M+H)$^+$.

Manufacturing Example 9: Manufacturing of Compound (1-14)

Compound (1-14) was manufactured as in Manufacturing Example 1 except that triazole compound (A-10) and thiazole compound (C-1) were used and was identified.
Result of Analysis of Compound (1-14)
[1] $^1$H-NMR (500 MHz, CDCl$_3$, room temperature): δ (ppm)=0.65-0.80 (3H, m), 0.84-1.18 (14H, m), 1.91-2.19 (2H, m), 2.86-3.00 (2H, m), 3.42-3.58 (2H, m), 3.80-3.95 (2H, m), 3.97-4.09 (1H, m), 4.22-4.31 (2H, m), 7.21-7.38 (3H, m), 7.39-7.50 (2H, m), 7.51-7.60 (2H, m), 7.61-7.68 (1H, m), 8.00 (2H, t, J=7.0 Hz).
[2] mass spectrometry (LCMS-2010): m/z=717.55 (M+H)$^+$.

Manufacturing of Ink

Inks of the present invention and inks for comparison were manufactured by the method described below.

Example 1: Manufacturing of Ink (1)

Five parts of a polyvinyl butyral resin (Denka 3000-K: manufactured by Denka Co., Ltd.) was gradually added to and dissolved in a mixture solution of 45 parts of methyl ethyl ketone and 45 parts of toluene. Furthermore, 5 parts of compound (1-1) synthesized in Manufacturing Example 1 was added to and dissolved in the resulting solution, thereby obtaining a cyan ink (1).

Examples 2 to 9: Manufacturing Inks (2) to (9)

Inks (2) to (9) were manufactured as in Example 1 except that compounds shown in Table 1 were used respectively instead of compound (1-1) in Example 1.

Comparative Examples 1 to 6: Manufacturing of Comparison Inks (1) to (6)

Comparison inks (1) to (6) were manufactured as in Example 1 except that comparative compounds (D-1) to (D-6) shown below were used respectively instead of compound (1-1) in Example 1.

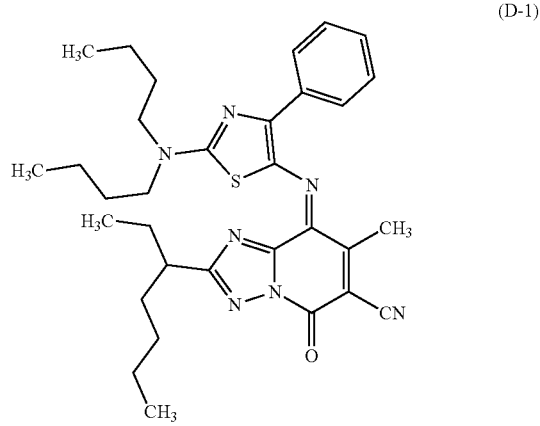

(D-1)

(D-2)
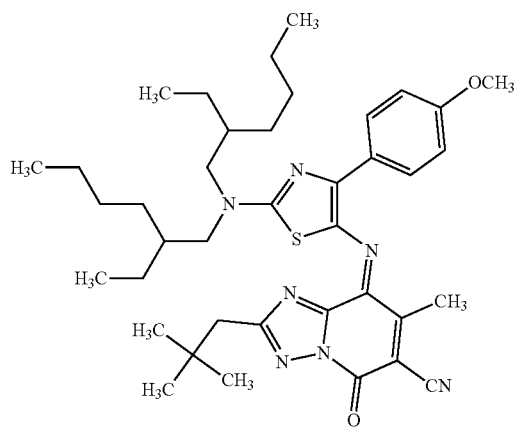

(D-3)
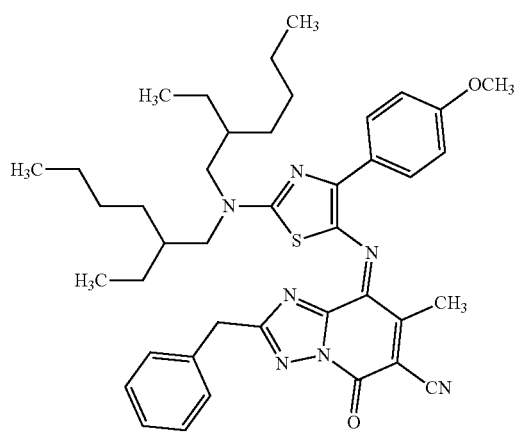

(D-4)
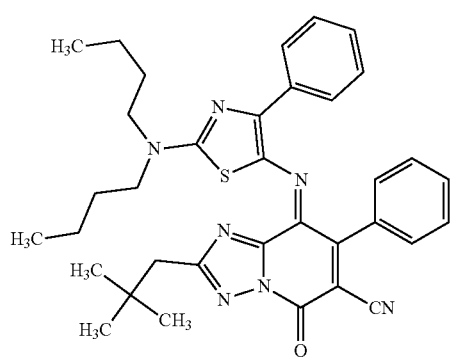

(D-5)
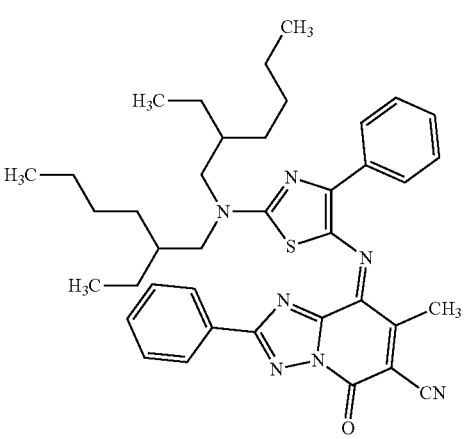

(D-6)
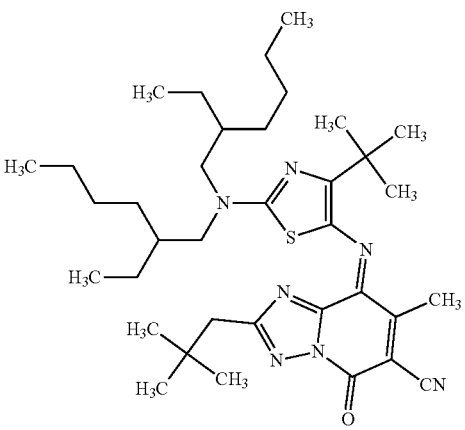

Production of Thermal Transfer Recording Sheet and Image Sample

The cyan ink (1) was applied onto a polyethylene terephthalate film (Lumirror (registered trademark): manufactured by Toray Industries, Ltd.) having a thickness of 4.5 μm such that the thickness after drying would be 1 μm and was dried, thereby producing a thermal transfer recording sheet using the ink of the present invention.

The thus-formed thermal transfer recording sheet was transferred to photographic paper using a modified apparatus of SELPHY manufactured by CANON KABUSHIKI KAISHA, thereby producing an image sample (1).

Evaluation of Chroma

Each of the produced image samples was measured for the chromaticity (L*, a*, b*) in the L*a*b* color system using a spectroscopic densitometer (fluorescence spectroscopic densitometer FD-7, manufactured by KONICA MINOLTA, INC.), and the chroma (C*) was calculated by the following expression.

$$C^* = \sqrt{(a^*)^2 (b^*)^2}$$

The larger both the chroma C* and the brightness L*, the more the increase in chroma, which means high chroma. The results are shown in Table 1. The evaluation criteria are as follows.

A: L* is 50.0 or more, and C* is 65.0 or more;

B: L* is 40.0 or more and less than 50.0, and C* is 65.0 or more; and

C: L* is less than 40.0, or C* is less than 65.0.

Aggregation Evaluation

Each of the produced image samples was observed with a phase-contrast microscope (BX53, manufactured by Olympus Corporation) to verify whether aggregates were present or not.
- A: There are no aggregates in the image sample;
- B: Aggregates are slightly observed in the image sample; and
- C: A large amount of aggregates are observed in the image sample.

Light Resistance Evaluation

The image samples were subjected to an exposure test for 5 hours using a xenon test device (Atlas Weather-Ometer Ci4000, manufactured by Toyo Seiki Seisaku-sho, Ltd.) under conditions of an illumination intensity of 0.28 W/m² at 340 nm, a black panel temperature of 40° C., and a relative humidity of 50%. When the initial optical density was defined as $OD_0$ and the O.D. after exposure for 5 hours was defined as $OD_5$, the O.D. survival rate was defined as follows, and evaluation was performed based on this value.

O.D. survival rate (%)=($OD_5$/$OD_0$)×100.

The evaluation criteria are as follows.
- A: An O.D. survival rate of 90% or more,
- B: An O.D. survival rate of 85% or more and less than 90%, and
- C: An O.D. survival rate of less than 85%.

The results are shown in Table 1.

dispersed using an attritor (manufactured by Nippon Coke & Engineering Co., Ltd.) for 1 hour, thereby obtaining an ink (1) for a resist composition.

Subsequently, 22 parts of the ink (1) for a resist composition was slowly added to a solution of 6.7 parts of an acrylic copolymer composition (weight average molecular weight Mw: 10,000) of a monomer rate of 40 mass % of n-butyl methacrylate, 30 mass % of acrylic acid, and 30 mass % of hydroxyethyl methacrylate, 1.3 parts of dipentaerythritol pentaacrylate, 0.4 parts of 2-benzyl-2-dimethylamino-1-(4-morpholinophenyl)-butanone (photopolymerization initiator), and 96 parts of cyclohexane, followed by stirring at room temperature for 3 hours. The resulting mixture was filtered with a filter of 1.5 μm, thereby obtaining a resist composition (1) for a color filter.

The resist composition (1) for a color filter was spin-coated on a glass substrate, dried at 90° C. for 3 minutes, then entirely exposed to light, and post cured at 180° C., thereby producing a color filter (1).

Examples 11 to 18

Resist compositions (2) to (9) for color filters were obtained as in Example 11 except that compounds shown in Table 2 were used respectively instead of compound (1-1). In addition, color filters (2) to (9) were produced using the

TABLE 1

| | | | Chroma | | | Aggregation | Light resistance evaluation | |
| | | | | | | | OD survival | |
| | | | c* | L* | Rank | evaluation | rate (%) | Rank |
|---|---|---|---|---|---|---|---|---|
| Example 1 | Compound (1-1) | Ink (1) | 72.9 | 50.4 | B | B | 87 | B |
| Example 2 | Compound (1-2) | Ink (2) | 73.0 | 50.4 | A | A | 93 | A |
| Example 3 | Compound (1-4) | Ink (3) | 74.4 | 50.5 | A | A | 92 | A |
| Example 4 | Compound (1-5) | Ink (4) | 69.1 | 55.9 | A | A | 91 | A |
| Example 5 | Compound (1-6) | Ink (5) | 65.9 | 61.5 | A | A | 87 | B |
| Example 6 | Compound (1-8) | Ink (6) | 69.3 | 58.5 | A | A | 96 | A |
| Example 7 | Compound (1-10) | Ink (7) | 73.0 | 53.7 | A | A | 98 | A |
| Example 8 | Compound (1-12) | Ink (8) | 73.8 | 52.0 | A | A | 97 | A |
| Example 9 | Compound (1-14) | Ink (9) | 71.8 | 55.4 | A | A | 98 | A |
| Comparative Example 1 | Comparative compound (D-1) | Comparative ink (1) | 76.3 | 47.6 | B | C | 79 | C |
| Comparative Example 2 | Comparative compound (D-2) | Comparative ink (2) | 70.0 | 60.1 | A | C | 77 | C |
| Comparative Example 3 | Comparative compound (D-3) | Comparative ink (3) | 71.3 | 59.5 | A | C | 75 | C |
| Comparative Example 4 | Comparative compound (D-4) | Comparative ink (4) | 73.0 | 50.4 | A | C | 69 | C |
| Comparative Example 5 | Comparative compound (D-5) | Comparative ink (5) | 60.4 | 63.2 | A | C | 60 | C |
| Comparative Example 6 | Comparative compound (D-6) | Comparative ink (6) | 52.2 | 54.2 | C | B | 40 | C |

As shown in Table 1, it was demonstrated that the inks of examples using the compounds represented by Formula (1) have excellent light resistance while maintaining high chroma compared to comparative inks.

Manufacturing of Color Filter

Resist compositions for color filters and color filters were manufactured by the methods described below.

Example 10

A mixture of 12 parts of compound (1-1) synthesized in Manufacturing Example 1 and 120 parts of cyclohexane was resulting resist compositions (2) to (9) for color filters by the same procedure as in Example 11.

Comparative Examples 7 to 12

Comparative resist compositions (1) to (7) for color filters were obtained as in Example 6 except that comparative compounds (D-1) to (D-7) were used respectively instead of compound (1-1). In addition, comparative color filters (1) to (7) were produced using the resulting comparative resist compositions (1) to (7) for color filters by the same procedure as in Example 6.

Evaluation of Chroma

A white sheet was placed under each of the color filters, and the chromaticity (L*, a*, b*) in the L*a*b* color system was measured using a spectroscopic densitometer (fluorescence spectroscopic densitometer FD-7, manufactured by KONICA MINOLTA, INC.), and the chroma (C*) was calculated by the above-mentioned expression. The evaluation criteria are the same as in Examples 1 to 5.

Light Resistance Evaluation

The color filters were subjected to an exposure test for 5 hours under conditions of an illumination intensity of 0.36 W/m² at 340 nm, a black panel temperature of 50° C., and a relative humidity of 50% using a xenon test device (Atlas Weather-Ometer Ci4000, manufactured by Toyo Seiki Seisaku-sho, Ltd.). Evaluation was performed according to the same evaluation criteria as in Example 1.

The results are shown in Table 2.

at the time of discharged was about 150° C.). The resulting kneaded product was cooled, roughly pulverized with a hammer mill, and then finely ground with a mechanical grinder (trade name: T-250, manufactured by Freund-Turbo Corporation) at a feeding amount of 20 kg/hr. Furthermore, the resulting finely pulverized product was classified using a multi-division classifier utilizing the Coanda effect, thereby obtaining toner particles.

Two parts of silica microparticles were externally added to 100 parts of the resulting toner particles with a Henschel mixer, thereby obtaining toner (1). The resulting toner had a weight average particle size (D4) of 5.8 μm and included 30.5% by number of particles having a particle size of 4.1 μm or less and 0.6% by volume of particles having a particle size of 10.1 μm or more.

The toner was applied at an amount of 0.45 mg/cm² on CLC color copy paper (manufactured by CANON KABU-

TABLE 2

|  |  |  | Chroma | | | Aggregation | Light resistance evaluation | |
|---|---|---|---|---|---|---|---|---|
|  |  |  | c* | L* | Rank | evaluation | OD survival rate (%) | Rank |
| Example 10 | Compound (1-1) | Color filter (1) | 71.8 | 50.3 | A | B | 86 | B |
| Example 11 | Compound (1-2) | Color filter (2) | 72.5 | 50.2 | A | A | 93 | A |
| Example 12 | Compound (1-4) | Color filter (3) | 73.4 | 50.3 | A | A | 92 | A |
| Example 13 | Compound (1-5) | Color filter (4) | 68.8 | 55.5 | A | A | 90 | A |
| Example 14 | Compound (1-6) | Color filter (5) | 65.0 | 60.9 | A | A | 88 | B |
| Example 15 | Compound (1-8) | Color filter (6) | 70.0 | 59.1 | A | A | 95 | A |
| Example 16 | Compound (1-10) | Color filter (7) | 73.2 | 54.2 | A | A | 98 | A |
| Example 17 | Compound (1-12) | Color filter (8) | 74.2 | 52.9 | A | A | 97 | A |
| Example 18 | Compound (1-14) | Color filter (9) | 72.0 | 56.0 | A | A | 99 | A |
| Comparative Example 8 | Comparative compound (D-1) | Comparative color filter (1) | 75.2 | 47.5 | B | C | 78 | C |
| Comparative Example 9 | Comparative compound (D-2) | Comparative color filter (2) | 68.9 | 58.8 | A | C | 77 | C |
| Comparative Example 10 | Comparative compound (D-3) | Comparative color filter (3) | 70.5 | 58.7 | A | C | 76 | C |
| Comparative Example 11 | Comparative compound (D-4) | Comparative color filter (4) | 72.2 | 48.7 | B | C | 68 | C |
| Comparative Example 12 | Comparative compound (D-5) | Comparative color filter (5) | 58.8 | 62.5 | C | C | 60 | C |
| Comparative Example 13 | Comparative compound (D-6) | Comparative color filter (6) | 51.8 | 53.4 | C | B | 38 | C |

Example 19

Binder resin (polyester resin): 100 parts
(Tg: 55° C., acid value: 20 mg KOH/g, hydroxyl value: 16 mg KOH/g, molecular weight: Mp 4,500, Mn 2,300, Mw 38,000)
C.I. Pigment Blue 15:3:5 parts
Compound (1-2): 0.5 parts
Aluminum 1,4-di-t-butylsalicylate compound: 0.5 parts
Paraffin wax (maximum endothermic peak temperature: 78° C.): 5 parts The materials above were thoroughly mixed with a Henschel mixer (trade name: Model FM-75J, manufactured by Nippon Coke & Engineering Co., Ltd.) and then kneaded with a twin-screw kneader (trade name: model PCM-45, manufactured by Ikegai Corp.) set to 130° C. at a feeding amount of 60 kg/hr (the temperature of the kneaded product SHIKI KAISHA) using a modified apparatus of LBP-5300 (manufactured by CANON KABUSHIKI KAISHA) to produce a fixed image. The chroma of the resulting image was measured with a spectroscopic densitometer (fluorescence spectroscopic densitometer FD-7, manufactured by KONICA MINOLTA, INC.) as the chromaticity (L*, a*, b*) in the L*a*b* color system. The obtained image had high chroma, C*=66 and L*=48.3.

The image above was subjected to a light resistance test as in Example 1, and the O.D. survival rate (%) was 96% or more.

Example 20

A toner (2) was obtained as in Example 19 except that compound (1-5) was used instead of compound (1-2) in Example 19. The resulting toner (2) was applied at an amount of 0.45 mg/cm² on CLC color copy paper (manufactured by CANON KABUSHIKI KAISHA) using a modified apparatus of LBP-5300 (manufactured by CANON KABUSHIKI KAISHA) to produce a fixed image. The obtained image had high chroma, C*=65 and L*=53.2. The image above was subjected to a light resistance test as in Example 1, and the O.D. survival rate (%) was 97% or more.

Example 21 toner (3) was obtained as in Example 19 except that compound (1-14) was used instead of compound (1-2) in Example 19. The resulting toner (3) was applied at an amount of 0.45 mg/cm² on CLC color copy paper (manufactured by CANON KABUSHIKI KAISHA) using a modified apparatus of LBP-5300 (manufactured by CANON KABUSHIKI KAISHA) to produce a fixed image. The chroma of the resulting image was measured with a spectroscopic densitometer (fluorescence spectroscopic densitometer FD-7, manufactured by KONICA MINOLTA, INC.) as the chromaticity (L*, a*, b*) in the L*a*b* color system. The obtained image had high chroma, C*=70 and L*=50.5. The image above was subjected to a light resistance test as in Example 1, and the O.D. survival rate (%) was 98% or more.

Formation of Thermal Transfer Recording Sheet
Preparation of Cyan Ink

Five parts of a polyvinyl butyral resin (Denka 3000-K: manufactured by Denka Co., Ltd.) was gradually added to and dissolved in a mixture solution of 45 parts of methyl ethyl ketone and 45 parts of toluene. Colorants were added to the resulting solution at the blending ratios shown in Table 3 in the total amount of 5 parts, thereby obtaining cyan inks (C1) to (C11) for forming thermal transfer recording sheets.

TABLE 3

| Cyan ink No. | Cyan dye included in Formula (1) | Cyan dye included in Formula (2) | Other cyan dye | Blending ratio (mass ratio) |
|---|---|---|---|---|
| C1 | Compound (1-5) | Compound (2-3) | — | 2:3:0 |
| C2 | Compound (1-2) | Compound (2-2) | — | 3:2:0 |
| C3 | Compound (1-1) | Compound (2-2) | — | 2:1:0 |
| C4 | Compound (1-4) | Compound (2-3) | — | 1:3:0 |
| C5 | Compound (1-6) | Compound (2-2) | — | 1:1:0 |
| C6 | Compound (1-8) | Compound (2-2) | — | 1:1:0 |
| C7 | Compound (1-10) | Compound (2-3) | — | 1:1:0 |
| C8 | Compound (1-12) | Compound (2-2) | — | 1:2:0 |
| C9 | Compound (1-14) | Compound (2-4) | — | 2:1:0 |
| C10 | — | — | Compound (D-1) | 0:0:1 |
| C11 | — | — | Compound (D-5) | 0:0:1 |

Preparation of Yellow Ink

Yellow inks (Y1) to (Y5) were prepared by the same method as the cyan inks by adding the yellow dyes at the blending ratios shown in Table 4 in the total amount of 4 parts.

TABLE 4

| Yellow ink No. | Yellow dye included in Formula (3) | Yellow dye included in Formula (4) | Yellow dye included in Formula (5) | Blending ratio (mass ratio) |
|---|---|---|---|---|
| Y1 | Compound (3-2) | Compound (4-5) | Compound (5-2) | 6:4:1 |
| Y2 | Compound (3-2) | Compound (4-3) | Compound (5-5) | 2:6:2 |
| Y3 | Compound (3-4) | Compound (4-4) | Compound (5-1) | 3:3:4 |
| Y4 | Compound (3-5) | Compound (4-3) | Compound (5-2) | 2:7:1 |
| Y5 | Compound (3-3) | Compound (4-5) | Compound (5-1) | 5:3:2 |

Preparation of Magenta Ink

Magenta inks (M1) to (M5) were prepared by the same method as the cyan inks by adding the magenta dyes at the blending ratios shown in Table 5 in the total amount of 5 parts.

TABLE 5

| Magenta ink No. | Magenta dye included in Formula (6) | Magenta dye included in Formula (7) | Magenta dye included in Formula (8) | Blending ratio (mass ratio) |
|---|---|---|---|---|
| M1 | Compound (6-1) | Compound (7-7) | Compound (8-1) | 3:2:5 |
| M2 | Compound (6-3) | Compound (7-3) | Compound (8-7) | 1:1:8 |
| M3 | Compound (6-3) | Compound (7-8) | Compound (8-3) | 3:3:4 |
| M4 | Compound (6-1) | Compound (7-3) | Compound (8-2) | 2:2:1 |
| M5 | Compound (6-3) | Compound (7-7) | Compound (8-7) | 1:1:3 |

Example 22

A polyethylene terephthalate film (trade name: Lumirror, manufactured by Toray Industries, Ltd.) having a thickness of 4.5 µm was used as a substrate, and the yellow ink (Y1) for forming a thermal transfer recording sheet was applied on the substrate such that the thickness after drying would be 1 µm and was dried, thereby forming a yellow layer.

Subsequently, a magenta layer was formed in a region adjacent to the yellow layer by the same method as the yellow layer except that the magenta ink (M1) was used instead of the yellow ink (Y1).

Similarly, a cyan layer was formed using the cyan ink (C1) in a region adjacent to the magenta layer. Thus, a first thermal transfer recording sheet including the yellow layer, the magenta layer, and the cyan layer was produced.

Using the produced thermal transfer recording sheet including the yellow layer, the magenta layer, and the cyan layer, an image was printed as a sample for color gamut evaluation with a modified apparatus of SELPHY (trade name) manufactured by CANON KABUSHIKI KAISHA by varying the printing output of each of Y, M, and C from 0% to 100% in increments of 12.5%.

In addition, the output was adjusted such that the optical density (O.D.) of each of yellow, magenta, and cyan in a printed product was 1.0. Furthermore, a black image was printed as a sample for imbalance evaluation by layering the inks in the order of yellow, magenta, and cyan at the adjusted output. Incidentally, the colorimetry of image sample was performed using a spectroscopic densitometer (fluorescence spectroscopic densitometer FD-7, manufactured by KONICA MINOLTA, INC.).

Examples 23 to 32 and Comparative Examples 13 and 14

Samples for color gamut evaluation and samples for imbalance evaluation of Examples 23 to 32 and Comparative Examples 13 and 14 were printed as in Example 22 except that the inks of the respective colors shown in Table 6 were used.

Evaluation

Evaluation of Color Gamut Volume

The chromaticity (L*, a*, b*) in the L*a*b* color system of primary color and secondary color parts of each image sample was measured using a spectroscopic densitometer (fluorescence spectroscopic densitometer FD-7, manufactured by KONICA MINOLTA, INC.).

The color gamut volume was simulated using the measurement results, and the percentage of improvement in the color gamut volume with respect to a standard was evaluated. Incidentally, Comparative Example 14 not using the compound (cyan dye) represented by Formula (1) was used as the standard.

The evaluation criteria of the color gamut volume are as follows. The results are shown in Table 6.

A: 120% or more,
B: 105% or more and less than 120%, and
C: less than 105%.

Imbalance Evaluation

The samples for imbalance evaluation were subjected to an exposure test for 10 hours under conditions of an illumination intensity of 0.28 W/m² at 340 nm, a temperature of 40° C., and a relative humidity of 50% using a xenon test device (trade name: Atlas Ci4000, manufactured by Atlas company).

When the initial optical density (O.D.) was defined as $OD_0$ and the O.D. after exposure for 10 hours was defined as $OD_{10}$, the O.D. survival rate was defined as follows. O.D. survival rate (%)=$OD_{10}/OD_0 \times 100$.

According to this expression, the O.D. survival rate of each of the cyan, magenta, and yellow components in the black image was calculated. The difference between the O.D. survival rates of the respective colors calculated by the following expressions was used as the indicator of imbalance, and this value was evaluated based on the following criteria.

$Bk_{C-Y}$=|[(yellow component O.D. survival rate)– (cyan component O.D. survival rate)]|

$Bk_{M-Y}$=|[(yellow component O.D. survival rate)– (magenta component O.D. survival rate)]|

$Bk_{C-M}$=|[(cyan component O.D. survival rate)–(magenta component O.D. survival rate)]|

Evaluation Criteria

A: 10 or less,
B: higher than 10 and 15 or less, and
C: higher than 15.

TABLE 6

| | Magenta ink | Yellow ink | Cyan ink | Color gamut Volume | Color gamut Rank | Imbalance $Bk_{C-Y}$ Value | Imbalance $Bk_{C-Y}$ Rank | Imbalance $Bk_{M-Y}$ Value | Imbalance $Bk_{M-Y}$ Rank | Imbalance $Bk_{C-M}$ Value | Imbalance $Bk_{C-M}$ Rank |
|---|---|---|---|---|---|---|---|---|---|---|---|
| Example 22 | M1 | Y1 | C1 | 128 | A | 7 | A | 8 | A | 1 | A |
| Example 23 | M2 | Y2 | C2 | 130 | A | 4 | A | 5 | A | 1 | A |
| Example 24 | M3 | Y3 | C3 | 122 | A | 11 | B | 12 | B | 2 | A |
| Example 25 | M4 | Y4 | C4 | 115 | B | 8 | A | 11 | A | 2 | A |
| Example 26 | M5 | Y5 | C5 | 125 | A | 6 | A | 9 | A | 2 | A |
| Example 27 | M2 | Y1 | C2 | 126 | A | 5 | A | 7 | A | 1 | A |
| Example 28 | M3 | Y2 | C3 | 128 | A | 6 | A | 7 | A | 1 | A |
| Example 29 | M1 | Y1 | C6 | 124 | A | 7 | A | 11 | A | 2 | A |
| Example 30 | M3 | Y4 | C7 | 126 | A | 6 | A | 9 | A | 2 | A |
| Example 31 | M5 | Y1 | C8 | 128 | A | 8 | A | 3 | A | 1 | A |
| Example 32 | M3 | Y4 | C9 | 122 | A | 4 | A | 8 | A | 1 | A |
| Comparative Example 13 | M1 | Y1 | C6 | 110 | B | 19 | C | 23 | C | 3 | A |
| Comparative Example 14 | M2 | Y2 | C7 | 100 | C | 23 | C | 25 | C | 4 | A |

The compound of the present invention has excellent light resistance while maintaining high chroma. Accordingly, the compound of the present invention can be suitably used as a colorant of an ink, a resist composition for a color filter, a thermal transfer recording sheet, and a toner.

The present invention is not limited to the above embodiments, and various changes and modifications can be made without departing from the spirit and scope of the present invention. Accordingly, the following claims are attached to make the scope of the present invention public.

According to the present invention, it is possible to provide a compound having excellent light resistance while maintaining high chroma. In addition, according to the present invention, it is possible to provide an ink, a resist composition for a color filter, a color filter, a thermal transfer recording sheet, and a toner having excellent high chroma and light resistance by using the compound having excellent light resistance while maintaining high chroma.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. A compound represented by formula (1):

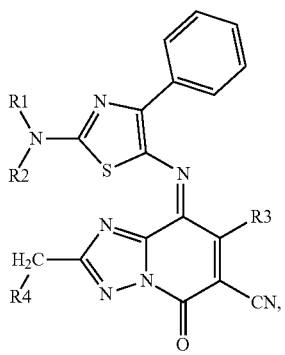

formula (1)

wherein, in the formula (1):
R1 and R2 represent 2-ethylhexyl groups;
R3 represents a linear alkyl group having 1 to 4 carbon atoms or a branched alkyl group having 3 or 4 carbon atoms; and
R4 represents a functional group selected from the group consisting of a t-butyl group, an iso-propyl group, a phenyl group, and a benzyl group.

2. The compound according to claim 1, wherein R4 in the formula (1) is a t-butyl group or a phenyl group.

3. An ink comprising a medium and the compound according to claim 1.

4. A resist composition for a color filter, comprising the compound according to claim 1.

5. A color filter comprising the compound according to claim 1.

6. A thermal transfer recording sheet comprising a substrate and a color material layer formed on the substrate, wherein the color material layer contains the compound according to claim 1.

7. A thermal transfer recording sheet comprising a substrate and a color material layer formed on the substrate, wherein the color material layer includes a yellow layer containing a yellow dye, a magenta layer containing a magenta dye, and a cyan layer containing a cyan dye,
wherein the yellow layer, the magenta layer, and the cyan layer are surface-sequentially stacked on the substrate, and
wherein the cyan dye contains the compound according to claim 1.

8. The thermal transfer recording sheet according to claim 7, wherein the cyan dye further contains a compound represented by formula (2):

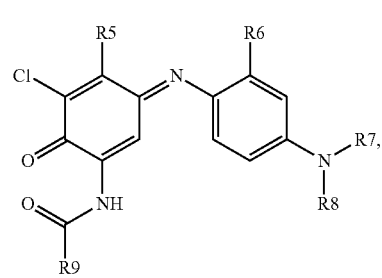

formula (2)

wherein, in the formula (2), R5 to R9 each independently represents an alkyl group or an aryl group.

9. The thermal transfer recording sheet according to claim 7, wherein the yellow dye contains one or more compounds selected from the group of compounds represented by formulae (3) to (5), and
wherein the magenta dye contains one or more compounds selected from the group of compounds represented by formulae (6) to (8):

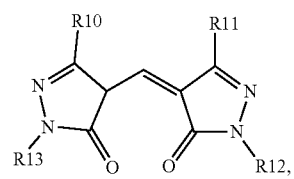

formula (3)

wherein, in the formula (3), R10 to R13 each independently represents an alkyl group or an aryl group optionally having a substituent;

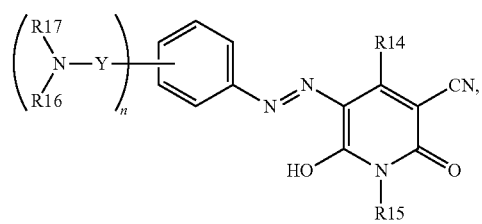

formula (4)

wherein, in the formula (4):
R14 represents an alkyl group, an aryl group optionally having a substituent, or an amino group optionally having a substituent;
R15 represents a hydrogen atom, an alkyl group, an aryl group optionally having a substituent, or —N(—$R^a$)$R^b$, where $R^a$ and $R^b$ each independently represents a hydrogen atom, an alkyl group, or an acyl group, and $R^a$ and $R^b$ may bind to each other to form a ring;
R16 represents an alkyl group;
R17 represents a hydrogen atom or an alkyl group;
Y represents a carbonyl group (—C(═O)—) or a sulfonyl group (—S(—O)$_2$—); and
n represents an integer of 1 to 3;

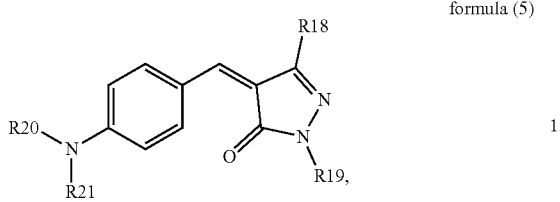

formula (5)

wherein, in the formula (5):
R18 represents an alkyl group, an aryl group, or an alkoxy group;
R19 represents an alkyl group or an aryl group; and
R20 and R21 each independently represents an alkyl group;

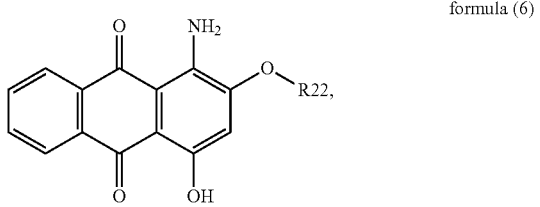

formula (6)

wherein, in the formula (6), R22 represents an unsubstituted alkyl group, an alkyl group substituted with an alkoxy group, or an aryl group optionally having a substituent;

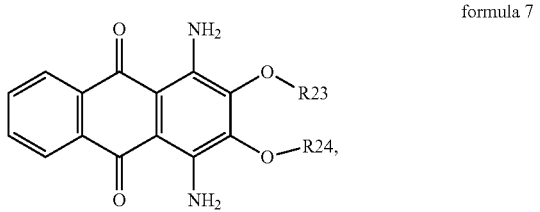

formula 7 wherein, in the formula (7), R23 and R24 each independently represents an alkyl group or an aryl group optionally having a substituent;

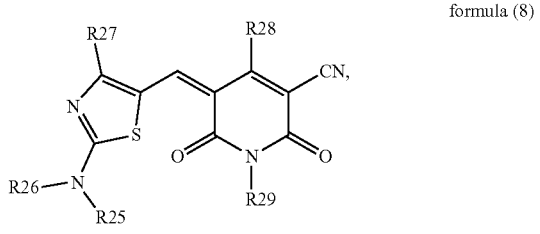

formula (8)

wherein, in the formula (8):
R25 and R26 each independently represents an alkyl group;
R27 represents a hydrogen atom, an alkyl group, or an aryl group optionally having a substituent;
R28 represents an alkyl group or an aryl group optionally having a substituent;
R29 represents a hydrogen atom, an alkyl group, an aryl group optionally having a substituent, or —N(—R30)R31, where R30 and R31 each independently represents a hydrogen atom, an alkyl group, an aryl group, or an acyl group or represent a cyclic structure formed by binding of R30 and R31 to each other.

10. A toner comprising a binder resin and a colorant, wherein the colorant contains the compound according to claim 1.

11. A toner comprising a binder resin and a colorant, wherein the colorant contains the compound according to claim 2.

12. An ink comprising a medium and the compound according to claim 2.

13. A resist composition for a color filter, comprising the compound according to claim 2.

14. A color filter comprising the compound according to claim 2.

15. A thermal transfer recording sheet comprising a substrate and a color material layer formed on the substrate, wherein the color material layer contains the compound according to claim 2.

16. A thermal transfer recording sheet comprising a substrate and a color material layer formed on the substrate,
wherein the color material layer includes a yellow layer containing a yellow dye, a magenta layer containing a magenta dye, and a cyan layer containing a cyan dye,
wherein the yellow layer, the magenta layer, and the cyan layer are surface-sequentially stacked on the substrate, and
wherein the cyan dye contains the compound according to claim 2.

17. The thermal transfer recording sheet according to claim 16, wherein the cyan dye further contains a compound represented by formula (2):

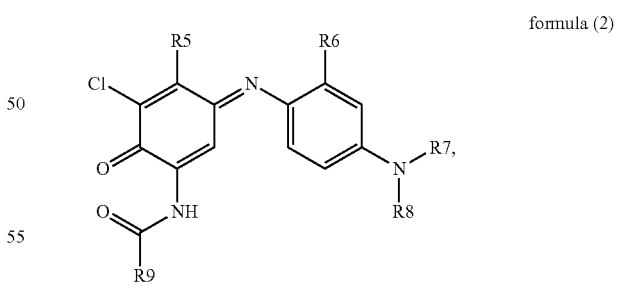

formula (2)

wherein, in the formula (2), R5 to R9 each independently represents an alkyl group or an aryl group.

18. The thermal transfer recording sheet according to claim 8, wherein the yellow dye contains one or more compounds selected from the group of compounds represented by formulae (3) to (5), and
wherein the magenta dye contains one or more compounds selected from the group of compounds represented by formulae (6) to (8):

formula (3)

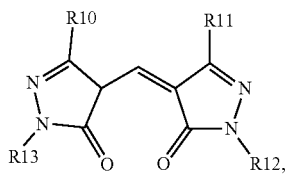

wherein, in the formula (3), R10 to R13 each independently represents an alkyl group or an aryl group optionally having a substituent;

formula (4)

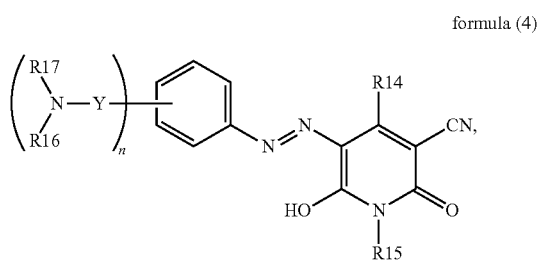

wherein, in the formula (4):

R14 represents an alkyl group, an aryl group optionally having a substituent, or an amino group optionally having a substituent;

R15 represents a hydrogen atom, an alkyl group, an aryl group optionally having a substituent, or —N(—$R^a$)$R^b$, where $R^a$ and $R^b$ each independently represents a hydrogen atom, an alkyl group, or an acyl group, and $R^a$ and $R^b$ may bind to each other to form a ring;

R16 represents an alkyl group;

R17 represents a hydrogen atom or an alkyl group;

Y represents a carbonyl group (—C(=O)—) or a sulfonyl group (—S(=O)$_2$-); and n represents an integer of 1 to 3;

formula (5)

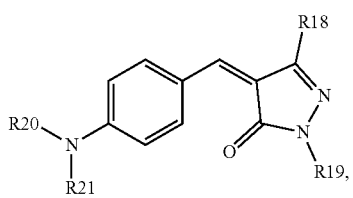

wherein, in the formula (5):

R18 represents an alkyl group, an aryl group, or an alkoxy group;

R19 represents an alkyl group or an aryl group; and

R20 and R21 each independently represents an alkyl group;

formula (6)

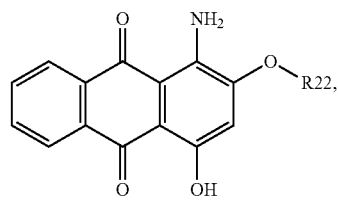

wherein, in the formula (6), R22 represents an unsubstituted alkyl group, an alkyl group substituted with an alkoxy group, or an aryl group optionally having a substituent;

formula (7)

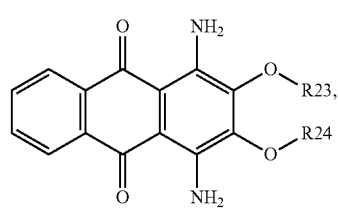

wherein, in the formula (7), R23 and R24 each independently represents an alkyl group or an aryl group optionally having a substituent;

formula (8)

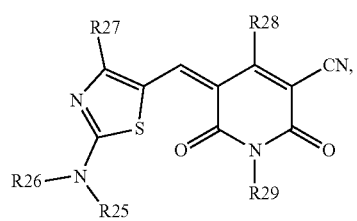

wherein, in the formula (8):

R25 and R26 each independently represents an alkyl group;

R27 represents a hydrogen atom, an alkyl group, or an aryl group optionally having a substituent;

R28 represents an alkyl group or an aryl group optionally having a substituent;

R29 represents a hydrogen atom, an alkyl group, an aryl group optionally having a substituent, or —N(—R30)R31, where R30 and R31 each independently represents a hydrogen atom, an alkyl group, an aryl group, or an acyl group or represent a cyclic structure formed by binding of R30 and R31 to each other.

19. The thermal transfer recording sheet according to claim 16, wherein the yellow dye contains one or more compounds selected from the group of compounds represented by formulae (3) to (5), and wherein the magenta dye contains one or more compounds selected from the group of compounds represented by formulae (6) to (8):

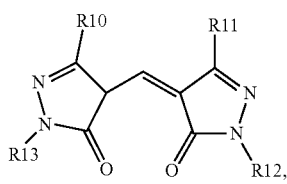

formula (3)

wherein, in the formula (3), R10 to R13 each independently represents an alkyl group or an aryl group optionally having a substituent;

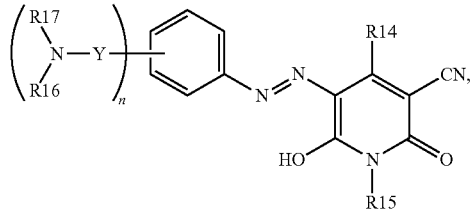

formula (4)

wherein, in the formula (4):
R14 represents an alkyl group, an aryl group optionally having a substituent, or an amino group optionally having a substituent;
R15 represents a hydrogen atom, an alkyl group, an aryl group optionally having a substituent, or —N(—R$^a$)R$^b$, where R$^a$ and R$^b$ each independently represents a hydrogen atom, an alkyl group, or an acyl group, and R$^a$ and R$^b$ may bind to each other to form a ring;
R16 represents an alkyl group;
R17 represents a hydrogen atom or an alkyl group;
Y represents a carbonyl group (—C(=O)—) or a sulfonyl group (—S(=O)$_2$—); and
n represents an integer of 1 to 3;

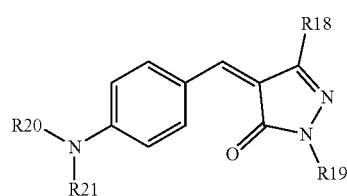

formula (5)

wherein, in the formula (5):
R18 represents an alkyl group, an aryl group, or an alkoxy group;
R19 represents an alkyl group or an aryl group; and
R20 and R21 each independently represents an alkyl group;

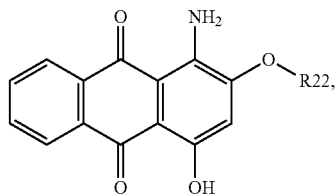

formula (6)

wherein, in the formula (6), R22 represents an unsubstituted alkyl group, an alkyl group substituted with an alkoxy group, or an aryl group optionally having a substituent;

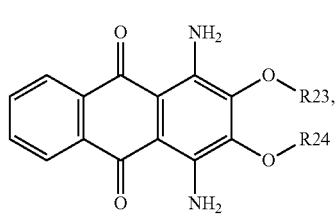

formula (7)

wherein, in the formula (7), R23 and R24 each independently represents an alkyl group or an aryl group optionally having a substituent;

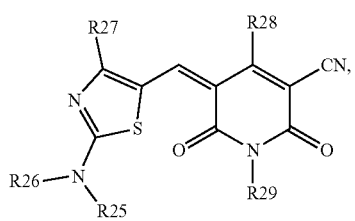

formula (8)

wherein, in the formula (8):
R25 and R26 each independently represents an alkyl group;
R27 represents a hydrogen atom, an alkyl group, or an aryl group optionally having a substituent;
R28 represents an alkyl group or an aryl group optionally having a substituent;
R29 represents a hydrogen atom, an alkyl group, an aryl group optionally having a substituent, or —N(—R30)R31, where R30 and R31 each independently represents a hydrogen atom, an alkyl group, an aryl group, or an acyl group or represent a cyclic structure formed by binding of R30 and R31 to each other.

20. The thermal transfer recording sheet according to claim 17, wherein the yellow dye contains one or more compounds selected from the group of compounds represented by formulae (3) to (5), and wherein the magenta dye contains one or more compounds selected from the group of compounds represented by formulae (6) to (8):

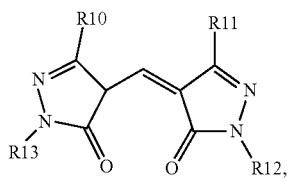

formula (3)

wherein, in the formula (3), R10 to R13 each independently represents an alkyl group or an aryl group optionally having a substituent;

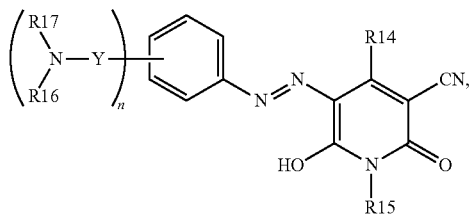

formula (4)

wherein, in the formula (4):
R14 represents an alkyl group, an aryl group optionally having a substituent, or an amino group optionally having a substituent;
R15 represents a hydrogen atom, an alkyl group, an aryl group optionally having a substituent, or —N(—$R^a$)$R^b$, where $R^a$ and $R^b$ each independently represents a hydrogen atom, an alkyl group, or an acyl group, and $R^a$ and $R^b$ may bind to each other to form a ring;
R16 represents an alkyl group;
R17 represents a hydrogen atom or an alkyl group;
Y represents a carbonyl group (—C(=O)—) or a sulfonyl group (—S(=O)$_2$—); and
n represents an integer of 1 to 3;

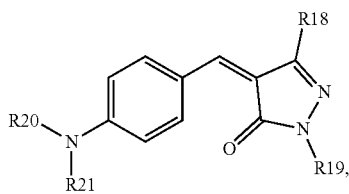

formula (5)

wherein, in the formula (5):
R18 represents an alkyl group, an aryl group, or an alkoxy group;
R19 represents an alkyl group or an aryl group; and
R20 and R21 each independently represents an alkyl group;

formula (6)

wherein, in the formula (6), R22 represents an unsubstituted alkyl group, an alkyl group substituted with an alkoxy group, or an aryl group optionally having a substituent;

formula (7)

wherein, in the formula (7), R23 and R24 each independently represents an alkyl group or an aryl group optionally having a substituent;

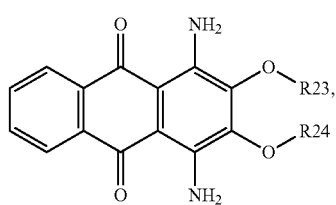

formula (8)

wherein, in the formula (8):
R25 and R26 each independently represents an alkyl group;
R27 represents a hydrogen atom, an alkyl group, or an aryl group optionally having a substituent;
R28 represents an alkyl group or an aryl group optionally having a substituent;
R29 represents a hydrogen atom, an alkyl group, an aryl group optionally having a substituent, or —N(—R30)R31, where R30 and R31 each independently represents a hydrogen atom, an alkyl group, an aryl group, or an acyl group or represent a cyclic structure formed by binding of R30 and R31 to each other.

* * * * *